US009365536B2

(12) United States Patent
Ohzawa et al.

(10) Patent No.: US 9,365,536 B2
(45) Date of Patent: Jun. 14, 2016

(54) METHOD FOR PRODUCING GLYCOLIDE, WHICH IS PROVIDED WITH RECTIFICATION STEP BY MEANS OF GAS-LIQUID COUNTERCURRENT CONTACT, AND METHOD FOR PURIFYING CRUDE GLYCOLIDE

(71) Applicant: Kureha Corporation, Tokyo (JP)

(72) Inventors: Takuya Ohzawa, Tokyo (JP); Naoki Hayashi, Tokyo (JP); Kentaro Otawara, Tokyo (JP); Kazuyuki Yamane, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/433,162

(22) PCT Filed: Nov. 19, 2013

(86) PCT No.: PCT/JP2013/081100
§ 371 (c)(1),
(2) Date: Apr. 2, 2015

(87) PCT Pub. No.: WO2014/080876
PCT Pub. Date: May 30, 2014

(65) Prior Publication Data
US 2015/0259320 A1    Sep. 17, 2015

(30) Foreign Application Priority Data

Nov. 22, 2012   (JP) ................................ 2012-256271

(51) Int. Cl.
*C07D 319/00* (2006.01)
*C07D 319/12* (2006.01)
*B01J 19/24* (2006.01)

(52) U.S. Cl.
CPC ............... *C07D 319/12* (2013.01); *B01J 19/24* (2013.01); *B01J 2219/00018* (2013.01); *B01J 2219/24* (2013.01)

(58) Field of Classification Search
CPC .................................................... C07D 319/12
USPC ........................................................ 549/274
See application file for complete search history.

(56) References Cited

U.S. PATENT DOCUMENTS

| | | | |
|---|---|---|---|
| 2,668,162 A | 2/1954 | Lowe | |
| 3,435,008 A | 3/1969 | Schmitt et al. | |
| 4,727,163 A | 2/1988 | Bellis | |
| 5,830,991 A | 11/1998 | Shiiki et al. | |
| 6,693,204 B2 * | 2/2004 | Ejiri | B01D 9/00 549/267 |
| 6,916,939 B2 * | 7/2005 | Yamane | C07D 319/12 203/39 |
| 7,235,673 B2 | 6/2007 | Yamane et al. | |
| 8,722,907 B2 | 5/2014 | Suzuki et al. | |
| 2003/0191326 A1 | 10/2003 | Yamane et al. | |
| 2004/0122240 A1 | 6/2004 | Yamane et al. | |
| 2008/0234500 A1 | 9/2008 | Meerdink et al. | |

FOREIGN PATENT DOCUMENTS

| | | |
|---|---|---|
| CN | 1432006 A | 7/2003 |
| CN | 1448209 A | 10/2003 |
| CN | 1894193 A | 1/2007 |
| CN | 1266146 C | 7/2008 |
| CN | 101887885 A | 10/2010 |
| EP | 1273579 A1 | 1/2003 |
| EP | 1550682 A1 | 7/2005 |
| EP | 2 377 858 A | 10/2011 |
| FR | 2692263 A1 | 12/1993 |
| JP | 63-152375 A | 6/1988 |
| JP | 09-328481 A | 12/1997 |
| JP | 2002-128777 A | 5/2002 |
| WO | WO 92/06969 A1 | 4/1992 |
| WO | WO/01/72736 A1 | 10/2001 |
| WO | WO/02/14303 A1 | 2/2002 |

(Continued)

OTHER PUBLICATIONS

English translation of International Preliminary Report on Patentability and Written Opinion issued Jun. 4, 2015, in PCT International Application No. PCT/JP2013/081100.
International Search Report of PCT/JP2013/081100 dated Feb. 10, 2014.
Second Office Action (including an English translation thereof) issued in the corresponding Chinese Patent Application No. 201380046913.0 on Mar. 31, 2016.

(Continued)

*Primary Examiner* — Nizal Chandrakumar
(74) *Attorney, Agent, or Firm* — Birch, Stewart, Kolasch & Birch, LLP

(57) ABSTRACT

A method for producing glycolide provided with: step (1) wherein a GAO composition, which preferably contains a high-boiling-point organic solvent or a solubilizing agent, is supplied into a reactor and heated to a temperature at which a depolymerization reaction of the GAO occurs; step (2) wherein the heating is continued to subject the GAO to the depolymerization reaction, thereby producing glycolide; step (3) wherein glycolide is distilled out of the reactor; step (4) wherein the distillate is introduced into a rectifier and is rectified by means of gas-liquid countercurrent contact; and step (5) wherein glycolide is recovered. A method for purifying crude glycolide provided with: step (i) wherein a crude glycolide composition, which preferably contains a high-boiling-point organic solvent or a solubilizing agent, is supplied into a reactor and heated so that glycolicde is distilled; step (ii) wherein the distillate is introduced into a rectifier and is rectified by means of gas-liquid countercurrent contact; and step (iii) wherein glycolide is recovered. A glycolide producing apparatus and a crude glycolide purifying apparatus, each of which is provided with a reactor and a rectifier.

12 Claims, 2 Drawing Sheets

(56) References Cited

FOREIGN PATENT DOCUMENTS

| | | |
|---|---|---|
| WO | WO/02/083661 A1 | 10/2002 |
| WO | WO/03/004126 A2 | 1/2003 |
| WO | WO/2006/114432 A2 | 11/2006 |
| WO | WO/2006/129736 A1 | 12/2006 |
| WO | WO/2010/073512 A1 | 7/2010 |

OTHER PUBLICATIONS

European Patent Office Communication and extended search report issued in the corresponding European Patent Application No. 13856470.3 on Mar. 8, 2016.

Chinese Office Action and Search Report, issued Oct. 21, 2015, for Chinese Application No. 201380045913.0, along with English translations.

* cited by examiner

METHOD FOR PRODUCING GLYCOLIDE, WHICH IS PROVIDED WITH RECTIFICATION STEP BY MEANS OF GAS-LIQUID COUNTERCURRENT CONTACT, AND METHOD FOR PURIFYING CRUDE GLYCOLIDE

TECHNICAL FIELD

The present invention relates to a method for producing high-purity glycolide efficiently and economically with long-term stability by means of the depolymerization of polyglycolic acid, and a method for purifying crude glycolide.

The glycolide obtained by the production method and purification method of the present invention is useful as a monomer for ring-opening polymerization for producing polyglycolic acid (may be called "PGA" hereafter). More specifically, the glycolide obtained by the production method of the present invention may be subjected to ring-opening polymerization alone or may be copolymerized with other comonomers to obtain polyglycolide (that is, polyglycolic acid) or various copolymers. Polyglycolic acid (copolymer) is useful as a biodegradable polymeric material, a polymeric material for medical use, and the like.

Further, the production method for glycolide according to the present invention can be applied to a method for producing glycolide via a low molecular weight polyglycolic acid such as a glycolic acid oligomer. In addition, the method for purifying crude glycolide according to the present invention is also useful as a method for recycling product waste, mold wastes or the like of high molecular weight polyglycolic acid by converting them into a glycolide monomer.

BACKGROUND ART

Aliphatic polyesters such as polyglycolic acid or polylactic acid are hydrolyzed in vivo and, in natural environments, are metabolized and degraded to water and carbon dioxide by microorganisms. Therefore, aliphatic polyesters have attracted attention as biodegradable polymeric materials which can be substituted for medical materials or commodity resins. Of these aliphatic polyester resins, polyglycolic acid has not only high biodegradability and hydrolyzability when an alkaline solution or the like, for example, is used, but also excellent mechanical characteristics such as heat resistance and tensile strength and, in particular, excellent gas barrier properties when used as a film or a sheet. Therefore, polyglycolic acid is expected to be used as agricultural materials, various packaging (container) materials, or polymeric materials for medical use, and applications have been expanded by using polyglycolic acid alone or combining polyglycolic acid with other resin materials or the like.

PGA can be synthesized by dehydrative polycondensation of glycolic acid serving as a monomer. However, with a polycondensation method using glycolic acid as a starting raw material, it is difficult to obtain high molecular weight PGA for use in a molding material or the like. Therefore, high molecular weight PGA is synthesized by performing ring-opening polymerization on a glycolide having the structure of a bimolecular cyclic ester of glycolic acid (may be called a "dimeric cyclic ester" hereafter) (that is, 1,4-dioxane-2,5-dione).

Specifically, PGA can be synthesized by dehydrating polycondensation of glycolic acid (that is, -hydroxyacetic acid) in accordance with the following formula [1]:

[Formula 1]

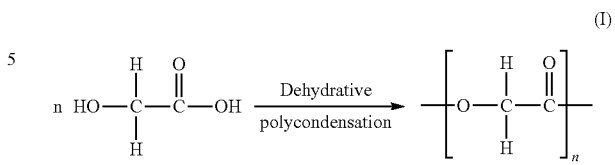

However, with a polycondensation method using glycolic acid as a starting raw material, it is difficult to obtain high molecular weight PGA. Therefore, high molecular weight PGA (that is, polyglycolide) is synthesized by performing ring-opening polymerization on glycolide having the structure of a bimolecular cyclic ester of glycolic acid in accordance with the following formula [II] in the presence of a catalyst such as tin octanoate.

[Formula 2]

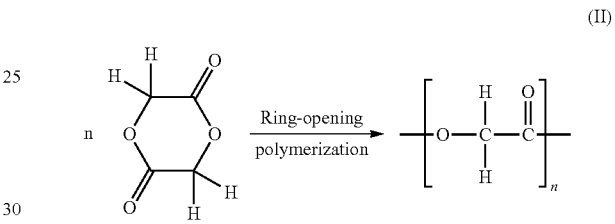

In order to mass-produce high molecular weight PGA on an industrial scale using glycolide as a raw material, it is indispensable to efficiently and economically supply high-purity glycolide. However, it was difficult to synthesize glycolide efficiently and economically. Glycolide is a dimeric cyclic ester with a structure in which two molecules of water are eliminated by an esterification reaction of two molecules of glycolic acid, but when glycolic acids are simply esterified with one another, a low molecular weight polymer such as a glycolic acid oligomer is ordinarily formed, and it is not possible to obtain glycolide as a dimeric cyclic ester with high yield. Therefore, a method of producing glycolide by synthesizing a glycolic acid oligomer and then depolymerizing the oligomer, for example, has been used.

The following is an example of a method conventionally known technique for obtaining a dimeric cyclic ester of -hydroxycarboxylic acid such as glycolide.

U.S. Pat. No. 2,668,162 (Patent Document 1) discloses a method of pulverizing a glycolic acid oligomer into a powder form, depolymerizing the ground product by heating to 270 to 285° C. in an ultra-vacuum of from 12 to 15 torr (1.6 to 2.0 kPa) while supplying the powder to a reaction vessel at a ratio of very small increments of approximately 20 g/hour, and then cooling, solidifying, and recovering the gaseous glycolide that is produced. In addition, Japanese Unexamined Patent Application Publication No. S63-152375A (Patent Document 2) discloses a method of using a polyether with excellent thermal stability as a substrate, performing block copolymerization on the substrate with a small amount of glycolic acid to form a block copolymer, and then depolymerizing the copolymer by heating so as to cool, solidify, and recover the gaseous glycolide. Further, U.S. Pat. No. 4,835,293 (Patent Document 3) discloses a method of heating a glycolic acid oligomer to form a melt, blowing an inert gas such as nitrogen gas onto the surface of the melt, making the glycolide that is produced and volatilized from the surface accompany the gas flow, and then cooling the gas flow to solidify and recover glycolide.

The glycolide obtained in this way contains impurities (primarily the glycolic acid oligomer that is used and the glycolic acid serving as a raw material thereof), so purification is conventionally performed by recrystallization using various different solvents such as, for example, isopropanol, t-amyl alcohol, carbon tetrachloride, and ethyl acetate. The slurry of crystalline glycolide obtained by recrystallization is washed with the solvent used in recrystallization or another washing solution while solid-liquid separation is performed by filtration, for example, and a purified crystal is obtained by then removing the solvent or the washing solution by drying.

However, such a purification method needs to include a drying step for removing the solvent or the washing solution from the crystal surface, a cooling and recovery step for the solvent or the washing solution removed in the drying step, and a distilled separation step for a mixture of the recovered solvent and washing solution, and these steps are intricate. Drying is performed at a temperature equal to or less than the melting point of the crystal, but since cyclic esters such as glycolide are sublimable, the crystal loss becomes large when the degree of depressurization is made too high at the time of drying. Further, impurities may also be incorporated into the crystal, and removing the impurities requires several cycles of recrystallization, which makes the step even more intricate.

On the other hand, there is also a known method of producing a cyclic ester such as glycolide using a high-boiling-point organic solvent. Japanese Unexamined Patent Application Publication No. H9-328481A (Patent Document 4) discloses a method of using a high-boiling-point organic solvent in a method for producing a dimeric cyclic ester of -hydroxycarboxylic acid by depolymerizing an -hydroxycarboxylic acid oligomer. This production method is a method of heating a mixture containing from 30 to 5,000 parts by weight of a high-boiling-point organic solvent per 100 parts by weight of an -hydroxycarboxylic acid oligomer to a temperature at which depolymerization occurs so as to form an essentially uniform solution phase, further continuing heating at the same temperature to distill out the dimeric cyclic ester that is produced together with the high-boiling-point organic solvent, and then recovering the dimeric cyclic ester from the distillate. With this method, it is possible to obtain a dimeric cyclic ester from an -hydroxycarboxylic acid oligomer with high yield while preventing the oligomer from becoming a tarry material. In addition, Patent Document 4 describes a method of purifying a crude dimeric cyclic ester of an -hydroxycarboxylic acid by applying the method described above.

Further, WO2002/14303 (Patent Document 5) discloses a production method for a cyclic ester, wherein:
(I) a mixture containing an aliphatic polyester (A) and a polyalkylene glycol ether (B), which is expressed by the following formula:

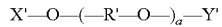

(wherein R' is a methylene group or a straight-chain or branched-chain alkylene group having from 2 to 8 carbon atoms, X' is a hydrocarbon group, Y' is an aryl group or alkyl group having from 2 to 20 carbon atoms, a is an integer of 1 or greater, and when a is 2 or greater, a plurality of R' moieties may be the same or different from one another) and has a boiling point of from 230 to 450° C. and a molecular weight of from 150 to 450, is heated to a temperature at which the depolymerization of the aliphatic polyester (A) occurs at normal pressure or reduced pressure;

(II) a substantially uniform solution phase is formed in which a melt phase of the aliphatic polyester (A) and a liquid phase consisting of the polyalkylene glycol ether (B);
(III) heating is continued in the solution state so as to produce the cyclic ester by depolymerization and distil out the cyclic ester together with the polyalkylene glycol ether (B); and
(IV) the cyclic ester is recovered from the distillate. According to this method, the cyclic ester produced by depolymerization is distilled off together with the polyalkylene glycol ether and both compounds are separated into distinct liquid phases to recover the cyclic ester phase, while the polyalkylene glycol ether phase without thermal deterioration may be circulated to the reaction system of depolymerization for its reuse. In addition, Patent Document 5 also describes a method of purifying a crude cyclic ester by applying the method described above.

Further, French Unexamined Patent Application Publication No. 2692263A (Patent Document 6) discloses a method of adding an oligomer of an -hydroxycarboxylic acid or an ester or salt thereof to a solvent containing a catalyst and stirring while heating to achieve catalytic decomposition. This method is performed at normal pressure or increased pressure using a solvent suitable for accompanying a cyclic ester in the gas phase, and the gas is condensed to recover the cyclic ester and the solvent. The Patent Document 6 illustrates a specific example in which a lactic acid oligomer is subjected to catalytic cracking using dodecane (boiling point: approximately 214° C.) as a solvent. However, when the present inventors conducted additional tests under the same conditions using a glycolic acid oligomer and dodecane, it was demonstrated that the formation of tarry material progresses simultaneously with the initiation of the depolymerization reaction and that the production of glycolide stops at a point when only a very small amount of glycolide has been produced. Moreover, the reaction residue was viscous, and cleaning required a substantial amount of labor. It is presumed that glycolide is susceptible to hardening by ring-opening polymerization within the device since it has higher reactivity than lactides.

With these methods, a dimeric cyclic ester of an -hydroxycarboxylic acid such as glycolide is distilled out together with a high-boiling-point organic solvent. The recovery of the cyclic ester such as glycolide from the distillate is performed by cooling the distillate, further adding a non-solvent of the cyclic ester such as glycolide as necessary, solidifying and precipitating the cyclic ester such as glycolide, and then performing solid-liquid phase separation. However, a crystal of a cyclic ester such as glycolide obtained in this way has low purity and not only contains impurities, but a high-boiling-point organic solvent that is difficult to remove by ordinary drying is deposited on the crystal, as described above. Therefore, in order to obtain a dry crystal with high purity, an operation of removing the organic solvent deposited on the crystal is essential in addition to the purification operation described above.

A conventional method of purifying a cyclic ester such as glycolide and removing an organic solvent deposited on the crystal is performed by substituting and washing the resulting crystal with a low-boiling-point washing solution such as cyclohexane or an ether and then removing the washing solution by drying. Drying is performed at a temperature equal to or less than the melting point of the crystal, but since cyclic esters such as glycolide are sublimable, the crystal loss becomes large when the degree of depressurization is made too high at the time of drying, and the yield of the cyclic ester such as glycolide decreases. Recrystallization is also sometimes further performed with ethyl acetate or the like as necessary, and the organic solvent deposited on the crystal is removed by drying at this time as well. Therefore, in a conventional method of purifying a crystal of a cyclic ester such as glycolide on which a high-boiling-point organic solvent is deposited, a new low-boiling-point washing solution becomes essential for substituting the organic solvent deposited on the crystal. As a result, the washing waste solution becomes a mixture of the high-boiling-point organic solvent and the low-boiling-point washing solution.

The aforementioned purification method for a crystal of a cyclic ester such as glycolide includes a drying step for removing the washing solution from the crystal surface, a recovery step for the washing solution removed by drying, and a purification and recovery step for the washing waste solution containing the high-boiling-point organic solvent and the low-boiling-point washing solution, and the steps are intricate. In addition, the washing solution that is used, such as alcohol, for example, may react with the cyclic ester and cause a transesterification reaction. Further, when impurities are incorporated into the crystal, several cycles of recrystallization are necessary, which makes the step even more intricate.

Therefore, in a method of producing glycolide by means of the depolymerization of a glycolic acid oligomer, there has been a demand for a method of producing a high-purity glycolide efficiently and economically, whereby complex purification operations can be reduced or, preferably made unnecessary.

WO2006/129736 (Patent Document 7) describes a method for producing a dimeric cyclic ester comprising two steps: [first step] a step in which a polymerization solution is obtained by adding alkylene glycol having a higher boiling point than the dimeric cyclic ester to be produced to at least one of an -hydroxycarboxylic acid such as glycolic acid and an -hydroxycarboxylic acid condensate such as glycolic acid condensate and performing a polymerization reaction; and [second step] a step in which the polymerization solution obtained in the first step is heated at normal pressure or reduced pressure, and a dimeric cyclic ester is obtained by performing a reaction and distillation simultaneously. As a specific example, a glycolic acid condensate is placed in a 500 ml flask, and polyethylene glycol is added (liquid, boiling point: 314° C., weight average molecular weight: approximately 400). The mixture of the glycolic acid condensate and the polyethylene glycol is then heated to 230° C. in a nitrogen atmosphere under reduced pressure conditions of 1.0 kPa so as to promote a polymerization reaction. A depolymerization reaction begins when heating is continued further, and the glycolide, which is a dimeric cyclic ester, is distilled out and accumulated in a receptacle. The second step then begins, wherein the mixture is heated at the temperature described above until the distillation of the glycolide substantially stops, and the glycolide is collected. It is described that when the content of the flask was observed after distillation was complete, a residue was present in the flask, and the deposition of the distillate was observed in the distillation line between the flask and the receptacle, but the amount of accumulation was minimal.

Polyglycolic acid is expected to be mass-produced and used in large quantities in the future, and the recycling of the product waste will be a critical issue. The recycling of molding wastes produced as a by-product at the time of the molding of polyglycolic acid will also become an issue. In a method of producing glycolide by means of the depolymerization of a glycolic acid oligomer, there is a demand for a method of stably producing high-purity glycolide efficiently and economically.

CITATION LIST

Patent Literatures

Patent Document 1: U.S. Pat. No. 2,668,162
Patent Document 2: Japanese Unexamined Patent Application Publication No. S63-152375A (corresponding to the specification of U.S. Pat. No. 4,727,163)
Patent Document 3: U.S. Pat. No. 4,835,293
Patent Document 4: Japanese Unexamined Patent Application Publication No. H9-328481A
Patent Document 5: WO2002/14303
Patent Document 6: French Unexamined Patent Application Publication No. 2692263A
Patent Document 7: WO2006/129736

SUMMARY OF INVENTION

Technical Problem

The problem of the present invention is to provide a method of stably producing high-purity glycolide efficiently and economically by means of the depolymerization of a glycolic acid oligomer, and a method for purifying crude glycolide efficiently and economically.

Solution to Problem

While conducting research to solve the problem described above, the present inventors discovered that in a method of producing glycolide by depolymerizing a glycolic acid oligomer, the glycolide produced by a depolymerization reaction by heating a glycolic acid oligomer composition containing a glycolic acid oligomer contains minute residual amounts of impurities such as free acids or solvents used in the depolymerization reaction in addition to glycolide, and the concentration of the free acids contained in the glycolide affects the stability of the produced glycolide over time and also affects the efficiency, economic viability, and long-run performance of the glycolide production method.

That is, when observing the effects of free acids remaining in the glycolide produced by the depolymerization reaction described above, the present inventors discovered that when free acids, including free carboxylic acids such as glycolic acid or glycolic acid dimers, are present in the produced glycolide, the oligomerization (formation of tarry material) of produced glycolide (hereafter, glycolide produced by a depolymerization reaction may be simply called "glycolide" hereafter) progresses in a short amount of time (at least approximately two hours). For example, it was determined that when glycolide containing glycolic acid as a free acid at a free acid concentration of 0.85 mmol/g (called "GL0.85" hereafter), glycolide containing glycolic acid at a free acid concentration of 0.16 mmol/g (called "GL0.16" hereafter), and glycolide containing no glycolic acid whatsoever (called "GL0.0" hereafter) were respectively stored in a nitrogen atmosphere at a temperature of 110° C. and the changes in the residual ratio (mass %) of glycolide were observed, as illustrated in FIG. 1, GL0.0 exhibited practically no mass loss even after 5 hours passed, and GL0.16 exhibited a mass loss of less than 5 mass % (residual ratio of at least 95 mass %), whereas GL0.85 exhibited a mass loss of over 35 mass % (residual ratio of at most 65 mass %). The residual ratio of glycolide was assessed based on the mass fraction (mass %) described below. Similarly, as illustrated in FIG. 2, it was determined that when the haze values after 5.5 hours passed were examined, GL0.0 and GL0.16 exhibited haze values of a level substantially lower than 1%, whereas GL0.85 exhibited a haze value of approximately 70%. Increases in haze values are presumed to be the result of the oligomerization of glycolide, so it was determined that glycolide in which free acids such as free carboxylic acid are present at a free acid concentration of approximately 0.85 mmol/g, is glycolide which is oligomerized, that is, the glycolide becomes a tarry material, after only a few hours and thus has poor stability over time and unsatisfactory practicability.

According to further research by the present inventors, it became clear that in a method of producing glycolide by depolymerizing a glycolic acid oligomer, the free acid concentration of the produced glycolide is preferably at most 0.6 mmol/g, more preferably at most 0.55 mmol/g, and even more preferably at most 0.52 mmol/g from the perspective of practicability.

The measurement method for the free acid concentration of glycolide and the measurement method for the haze value of glycolide are as follows.

(Measurement of the Free Acid Concentration of Glycolide)

The free acid concentration in glycolide is measured with the following method. Specifically, 30 mg of a glycolide sample is dissolved in a mixed solvent of 25 ml of acetone and 25 ml of methanol. A methanol solution containing sodium methoxide is dropped into the solution as a neutralizing solution, and the point of neutralization is detected. The free acid concentration present in 1 g of the glycolide sample is calculated from the detected point of neutralization as the number of mmol (units: mmol/g).

(Measurement of Changes in the Residual Ratio and Haze Value of Glycolide Over Time)

The measurement of changes in the residual rate (mass fraction) and haze value of glycolide over time was performed with the following method. Specifically, glycolide (purity: at least 99.96 mass %) and a prescribed amount of glycolic acid were added to a sample vial with a volume of 10 ml, and after nitrogen was sealed in the vial, the vial was immersed in an oil bath and left to stand at a temperature of 110° C. At points when prescribed amounts of time had passed after the sample vial was first left to stand in the oil bath (1.5 hours, 3.5 hours, and 5.5 hours after the test was begun), the sample vial was cooled to room temperature, and a 100 mg sample including glycolide and a prescribed amount of glycolic acid was collected. The residual ratio and the haze value of glycolide were measured for each sample, and the changes in the values over time were determined.

(Measurement of the Residual Ratio of Glycolide)

The residual ratio of glycolide was measured with the following method. Specifically, 100 mg of a sample containing glycolide and a prescribed amount of glycolic acid that were collected at the points after the prescribed amounts of time described above had passed and 40 mg of p-chlorobenzophenone (made by Tokyo Chemical Industry Co., Ltd.) serving as an internal standard substance were dissolved in 10 ml of acetone. Next, 2 μl of the solution was collected and injected into a gas chromatography device, and the amount of glycolide was measured. A calibration curve created in advance using glycolide and p-chlorobenzophenone serving as the internal standard substance was used to determine the purity of the glycolide remaining in the sample. Next, the residual ratios of glycolide at the points after the prescribed amounts of time described above had passed were calculated by the following equation.

Residual ratio of glycolide(mass %)=$(a/b) \times 100$ a: mass of glycolide remaining in the sample (g)
b: mass of glycolide initially added to the sample vial(g)

(Measurement of the Haze Value of Glycolide)

The haze value of glycolide was measured using a Water Analyzer 2000N (made by Nippon Denshoku Industries Co., Ltd.). Specifically, 100 mg of a sample containing glycolide and a prescribed amount of glycolic acid that were collected as described above was completely dissolved in 20 ml of acetone using an ultrasonic vibrator in an erlenmeyer flask with a volume of 50 ml. The dissolved sample was added to an analysis cell, and the haze values (units: %) were measured at the points after the prescribed amounts of time described above had passed.

While conducting further research into a glycolide production method with which glycolide having excellent practicability as a result of a free acid concentration of at most 0.6 mmol/g can be obtained while taking the above knowledge into consideration, the present inventors discovered that in a method of producing glycolide by depolymerizing a glycolic acid oligomer, the problem described above can be solved by introducing glycolide, which is produced by heating a glycolic acid oligomer composition, preferably a glycolic acid oligomer composition containing a glycolic acid oligomer and a high-boiling-point organic solvent having a boiling point within a range of 220 to 500° C. at normal pressure, into a rectifier and rectifying the glycolide by means of gas-liquid countercurrent contact, and the present inventors thereby completed the present invention.

In addition, the present inventors discovered that the problem can be solved by heating a crude glycolide composition, introducing the composition into a rectifier, and rectifying the composition by means of gas-liquid countercurrent contact, and the present inventors thereby completed the present invention.

That is, the present invention provides a method for producing glycolide by depolymerizing a glycolic acid oligomer, the method comprising the following steps (1) to (5):

step (1): a step in which a glycolic acid oligomer composition is supplied into a reactor and heated to a temperature at which a depolymerization reaction of the glycolic acid oligomer occurs at normal pressure or reduced pressure;

step (2): a step in which heating is continued and the depolymerization reaction of the glycolic acid oligomer occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

The present invention provides the following methods (I) to (XI) for producing glycolide as embodiments.

(I) The aforementioned method for producing glycolide, wherein the glycolic acid oligomer composition is a glycolic acid oligomer composition containing a glycolic acid oligomer and a high-boiling-point organic solvent having a boiling point within a range of 220 to 500° C. at normal pressure.

(II) The aforementioned method for producing glycolide, wherein step (3) is a step in which the produced glycolide is distilled out of the reactor together with the high-boiling-point organic solvent.

(III) The aforementioned method for producing glycolide, wherein the high-boiling-point organic solvent is at least one type selected from the group consisting of aromatic alkoxyalkyl carboxylate esters, aliphatic alkoxyalkyl carboxylate esters, polyalkylene glycol ethers, polyalkylene glycol esters, aromatic carboxylic acid esters, aliphatic carboxylic acid esters, aromatic ethers, aliphatic ethers, aromatic phosphoric acid esters, aliphatic phosphoric acid esters, aliphatic imide compounds, aliphatic amide compounds, and aromatic halides.

(IV) The aforementioned method for producing glycolide, wherein the high-boiling-point organic solvent forms a liquid phase substantially uniform with a melt phase of the glycolic acid oligomer in the step (1).

(V) The aforementioned method for producing glycolide, wherein the high-boiling-point organic solvent is at least one type of a polyalkylene glycol ether represented by formula (1):

$$X-O-(-R-O-)_p-Y \qquad (1)$$

(wherein R is a methylene group or a straight-chain or branched-chain alkylene group having from 2 to 8 carbon atoms, X and Y are each independently a methyl group or an alkyl group or an aryl group having from 2 to 20 carbon atoms, p is an integer of 1 or greater, and when p is 2 or greater, a plurality of R moieties may be the same or different from one another).

(VI) The aforementioned method for producing glycolide, wherein the glycolic acid oligomer composition is a glycolic acid oligomer composition containing a solubilizing agent.

(VII) The aforementioned method for producing glycolide, wherein the solubilizing agent is a monohydric or polyhydric alcohol or a phenol compound having a boiling point of at least 190° C. at normal pressure.

(VIII) The aforementioned method for producing glycolide, wherein in the step (2), a depolymerization reaction is performed at a temperature within a range of 180 to 320° C. and a pressure within a range of 0.1 to 90 kPa.

(IX) The aforementioned method for producing glycolide, wherein at least one of the high-boiling-point organic solvent and a solubilizing agent which is separated in at least one of the step (4) and the step (5) and has a boiling point within a range of 220 to 500° C. at normal pressure is refluxed to the reactor.

(X) The aforementioned method for producing glycolide, wherein the step (4) is implemented using a rectifier disposed so as to be connected to the reactor.

(XI) The aforementioned method for producing glycolide, wherein the glycolic acid oligomer composition is a glycolic acid oligomer composition not containing a high-boiling-point organic solvent having a boiling point within a range of 220 to 500° C. at normal pressure.

Further, the present invention provides a method for purifying crude glycolide comprising the following steps (i) to (iii):

step (i): a step in which a crude glycolide composition is supplied into a reactor and heated at normal pressure or reduced pressure so that glycolide is distilled;

step (ii): a step in which the distillate is introduced into a rectifier and is rectified by means of gas-liquid countercurrent contact; and step (iii): a step in which glycolide is recovered.

Further, the present invention provides the following methods (A) to (C) for purifying crude glycolide as embodiments.

(A) The aforementioned method for purifying crude glycolide, wherein the crude glycolide composition is a crude glycolide composition containing crude glycolide and a high-boiling-point organic solvent having a boiling point within a range of 220 to 500° C. at normal pressure, and
the step (i) is a step in which glycolide is distilled out together with the high-boiling-point organic solvent.

(B) The aforementioned method for purifying crude glycolide, wherein the crude glycolide composition is a crude glycolide composition containing a solubilizing agent.

(C) The aforementioned method for purifying crude glycolide, wherein at least one of the high-boiling-point organic solvent and a solubilizing agent which is separated in at least one of step (ii) and step (iii) and has a boiling point within a range of 220 to 500° C. at normal pressure is refluxed to the reactor.

In addition, the present invention provides an apparatus for producing glycolide comprising a reactor and a rectifier and provides an apparatus for purifying crude glycolide comprising a reactor and a rectifier.

Advantageous Effects of Invention

The present invention is a method for producing glycolide by depolymerizing a glycolic acid oligomer, the method comprising the following steps (1) to (5):

step (1): a step in which a glycolic acid oligomer composition is supplied into a reactor and heated to a temperature at which a depolymerization reaction of the glycolic acid oligomer occurs at normal pressure or reduced pressure;

step (2): a step in which heating is continued and the depolymerization reaction of the glycolic acid oligomer occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

Therefore, the concentration of free acids in the glycolide distillate can be reduced, which yields the effect of being capable of providing a method for producing high-purity glycolide having excellent efficiency, economic viability, and long-run performance.

In particular, the present invention provides the aforementioned method for producing glycolide by depolymerizing a glycolic acid oligomer, wherein the glycolic acid oligomer composition is a glycolic acid oligomer composition containing a glycolic acid oligomer and a high-boiling-point organic solvent having a boiling point within a range of 220 to 500° C. at normal pressure, and the step (3) is more preferably a step in which the produced glycolide is distilled out of the reactor together with the high-boiling-point organic solvent. Therefore, the concentration of free acids in the glycolide distillate can be reduced, which yields the effect of being capable of providing a method for producing high-purity glycolide having even better efficiency, economic viability, and long-run performance.

Specifically, the method for producing glycolide by depolymerizing a glycolic acid oligomer according to the present invention yields the following effects:

i) Glycolide with high purity can be recovered as the glycolide that is obtained. As a result, the production efficiency as a method for producing glycolide improves, and after-treatment such as crystallization or recrystallization that was conventionally required becomes easy or, depending on the situation, treatment such as crystallization or recrystallization can be omitted, so the glycolide yield improves.

ii) Even if the production of glycolide by means of a depolymerization reaction of a glycolic acid oligomer is continued for a long period of time, the accumulation of the transformation of glycolic acid into a tarry material or by-products in the depolymerization reaction system is suppressed, and decreases in the production rate of glycolide can be suppressed, which enables long-run operation. As a result, it is possible to minimize decreases in production efficiency due to the interruption of the production of glycolide or the cleaning of the depolymerization reaction device or the like, or decreases in thermal efficiency due to repeated heating and cooling.

iii) Most of the heat expended for depolymerization, including the distillation of the high-boiling-point organic solvent, can be used as heat for implementing the rectification step and can be recovered, which saves energy and contributes to the prevention of global warming.

iv) The rectification step may also be performed by replacing the distillation system that was provided conventionally, so the design or scale-up is easy, and mass production on an industrial scale is also easy. Further, integrating the reactor and the rectifier eliminates the need to separately install distillation equipment, which contributes to space conservation, equipment conservation, resource conservation, and cost conservation.

v) In particular, since the method for producing glycolide is one in which the glycolic acid oligomer composition is a glycolic acid oligomer composition containing a glycolic acid oligomer and a high-boiling-point organic solvent having a boiling point within a range of 220 to 500° C. at normal pressure, and the produced glycolide is even more preferably distilled out of the reactor together with the high-boiling-point organic solvent, the concentration of free acids in the resulting glycolide can be further reduced, which makes it possible to provide a method for producing glycolide having even better efficiency, economic viability, and long-run performance.

vi) In addition, by inducing the depolymerization of a glycolic acid oligomer with a solution phase and preferably a uniform solution phase, the surface area of the glycolic acid oligomer increases, and the contact between glycolic acid oligomers is suppressed by the diluting effect of the solvent, so the production rate of glycolide produced by the depolymerization reaction from the glycolic acid oligomer surface increases.

vii) Further, the high-boiling-point organic solvent causes practically no thermal degradation in the depolymerization reaction and the distillation step, so the solvent used in the depolymerization reaction can be used again in another depolymerization reaction, and the amount of solvent that needs to be newly replenished during continuous operation can be made very small. Accordingly, when mass-producing cyclic esters, the solvent cost can be dramatically reduced, which, as a result, yields the effect that cyclic esters such as glycolide can be mass-produced at low cost.

Further, the method for purifying crude glycolide according to the present invention is a method for purifying crude glycolide comprising the following steps (i) to (iii):

step (i): a step in which a crude glycolide composition is supplied into a reactor and heated at normal pressure or reduced pressure so that glycolide is distilled;
step (ii): a step in which the distillate is introduced into a rectifier and is rectified by means of gas-liquid countercurrent contact; and
step (iii): a step in which glycolide is recovered.

This yields the effect that it is possible to provide a method for purifying crude glycolide capable of obtaining, with high yield, glycolide with little or no impurity content and a reduced free acid concentration.

In addition, the apparatus for producing glycolide or the apparatus for purifying crude glycolide according to the present invention is an apparatus for producing glycolide or an apparatus for purifying crude glycolide comprising a reactor and a rectifier, which yields the effect that it is possible to provide an apparatus for producing glycolide or an apparatus for purifying crude glycolide capable of continuing a reaction for a long period of time without any decrease in production efficiency and capable of efficiently and economically producing glycolide with high purity, reduced impurities such as free acids, and excellent stability by depolymerizing a glycolic acid oligomer, or purifying crude glycolide.

DESCRIPTION OF EMBODIMENTS

1. Glycolic Acid Oligomer

Figure 1:
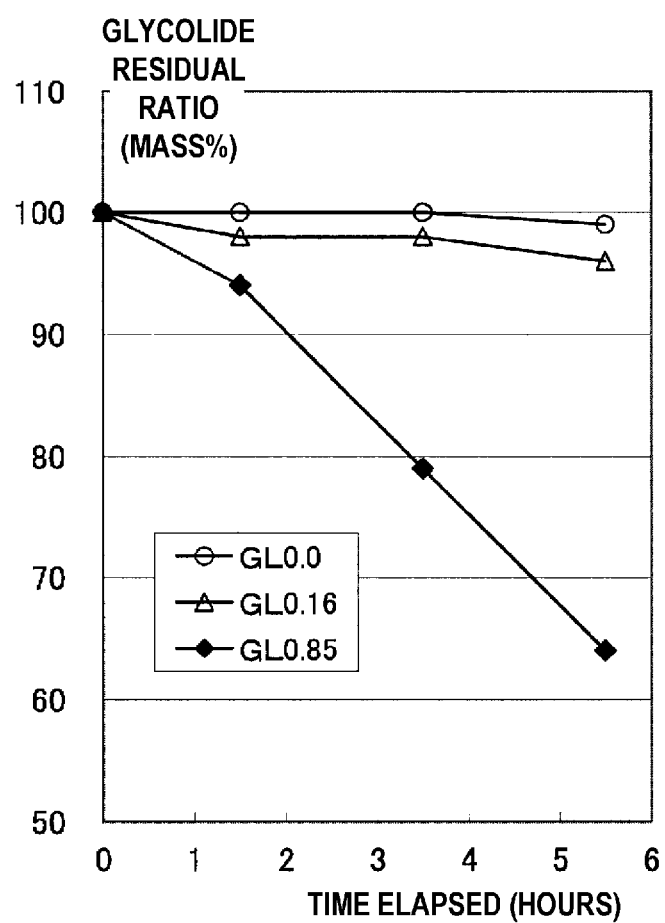
FIG. 1 illustrates the relationship between the free acid concentration of glycolide and changes in the residual ratio of glycolide over time.
Figure 2:
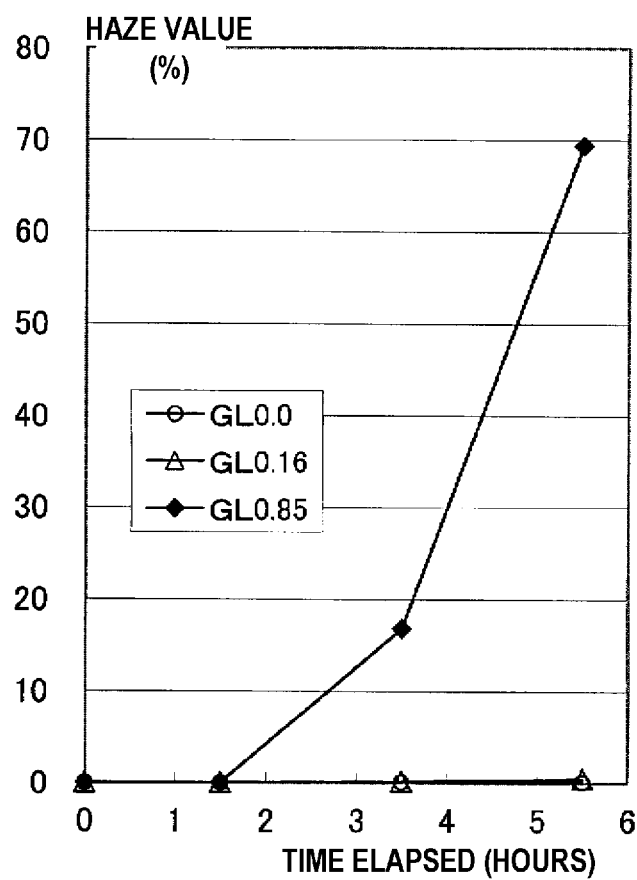
FIG. 2 illustrates the relationship between the free acid concentration of glycolide and changes in the haze value of glycolide over time.

The method for producing glycolide according to the present invention is a method for producing glycolide by depolymerizing a glycolic acid oligomer. The glycolic acid oligomer (may be called "GAO" hereafter) used in the present invention is a polymer or copolymer of glycolic acid containing repeating units capable of producing glycolide by means of depolymerization. Such a GAO can be obtained by (co)polycondensation using glycolic acid or an alkyl ester or salt thereof or can be obtained by ring-opening (co)polymerization using glycolide as a monomer.

The GAO used in the present invention is a (co)polymer having a weight average molecular weight of at least 3,000, in many cases at least 5,000, preferably at least 8,000, and more preferably at least 10,000. The upper limit of the weight average molecular weight of the GAO is ordinarily approximately 80,000 and in many cases approximately 50,000. The weight average molecular weight is a value measured using gel permeation chromatography (GPC) and can be measured as a standard polymethylmethacrylate (PMMA) reduced value by means of GPC measurement using hexafluoroisopropanol (HFIP) as a solvent.

The GAO may be a copolymer of glycolic acid. Examples of comonomers that can be copolymerized with glycolic acid include lactic acid and -hydroxycarboxylic acids such as -hydroxybutyric acid and -hydroxyvaleric acid, and dimeric cyclic esters thereof may also be used. When the GAO is a copolymer of glycolic acid, it is desirably a copolymer in which the content of repeating units of glycolic acid is at least 50 mass %, preferably at least 80 mass %, more preferably at least 90 mass %, and even more preferably at least 95 mass %.

The GAO can be synthesized in accordance with a conventional method. For example, glycolic acid or an ester or salt thereof and a comonomer used as necessary are heated in the presence of a transesterification catalyst or condensation catalyst as necessary at reduced pressure or increased pressure at a temperature of from 100 to 250° C. and preferably from 140 to 230° C., and a condensation reaction or transesterification reaction is performed until the distillation of low molecular weight substances such as water or alcohol is essentially eliminated. After the condensation reaction or the transesterification reaction is complete, the produced GAO can be used directly as a raw material for depolymerization according to the present invention. In addition, the obtained GAO may be extracted from the reaction system, washed with a non-solvent such as benzene or toluene, and used after unreacted matter, catalysts, and the like are removed. The structure of the GAO may be cyclic or straight-chained. Other GAOs may also be synthesized with the same method.

The GAO may have a low degree of polymerization, but the melting point (Tm) is ordinarily at least 140° C., preferably at least 160° C., and more preferably at least 180° C. from the perspective of the yield of glycolide at the time of depolymerization. Here, Tm is the melting point detected when heated at a rate of 20° C./min in an inert gas atmosphere using a differential scanning calorimeter (DSC).

The GAO used to produce glycolide by means of depolymerization can also be synthesized by the ring-opening (co) polymerization of glycolide, but waste matter of used PGA products, molding wastes, or the like can be suitably used, and this enables recycling. The shapes of the used PGA products are not particularly limited, and any shapes such as a sheet shape, a film shape, a thread shape, a spherical shape, a columnar shape, or a rod shape, for example, can be used. It is preferable from the perspective of increasing the reaction efficiency to prepare these products into a granular shape, a powder, or a fiber, or the like prior to a depolymerization reaction. For this purpose, the products can be used in a depolymerization reaction after being granulated or powderized by pulverization, melting, or the like or processed into a fiber shape by melting or drawing.

In the present invention, the GAO may be supplied all at once into a reactor such as a reaction vessel prior to the depolymerization reaction, or it may be supplied by continuous addition or divided addition during the depolymerization reaction. However, as described above, during the depolymerization reaction, the residual ratio of the melt phase of the GAO in the reactor is preferably set to at most 0.5, and the GAO in the reactor is preferably one capable of forming a phase substantially uniform with the melt phase of the GAO and the high-boiling-point organic solvent (solution state). In this case, a backup reactor may be provided separately so that the melt phase of the GAO and the liquid phase of the high-boiling-point organic solvent form a more uniform phase, and after the uniform phase is formed, it may be introduced into the reactor for performing depolymerization. Further, a substantially uniform phase may also be formed by further including the solubilizing agent described below.

2. High-Boiling-Point Organic Solvent

The method for producing glycolide by depolymerizing a GAO according to the present invention is a method for producing glycolide comprising the following steps (1) to (5):

step (1): a step in which a GAO composition is supplied into a reactor and heated to a temperature at which a depolymerization reaction of the GAO occurs at normal pressure or reduced pressure;
step (2) a step in which heating is continued and the depolymerization reaction of the GAO occurs, thereby producing glycolide;
step (3): a step in which the produced glycolide is distilled out of the reactor;
step (4): a step in which the distillate is introduced into a rectifier and is rectified by means of gas-liquid countercurrent contact; and
step (5): a step in which glycolide is recovered.

The method for producing glycolide by depolymerizing a GAO according to the present invention is preferably a production method for glycolide in which the GAO composition is a GAO composition containing a GAO and a high-boiling-point organic solvent having a boiling point within a range of 220 to 500° C. at normal pressure (may be simply called a "high-boiling-point organic solvent" hereafter).

When the boiling point of the high-boiling-point organic solvent at normal pressure is too low, it is not possible to set the GAO depolymerization reaction temperature to a high temperature, and as a result, the production rate of glycolide may decrease. On the other hand, when the boiling point of the high-boiling-point organic solvent at normal pressure is too high, the high-boiling-point organic solvent becomes difficult to distill, and the effect of rectifying the glycolide that is distilled out by means of gas-liquid countercurrent contact may not be sufficiently expressed. In addition, the co-distillation from the reactor with the glycolide produced by the depolymerization reaction described below may become difficult. The boiling point of the high-boiling-point organic solvent at normal pressure is within a range of 220 to 500° C., preferably within a range of 230 to 470° C., and more preferably within a range of 240 to 450° C.

In the present invention, the rectification step is preferably performed in the presence of a high-boiling-point organic solvent so as to prevent situations in which the production of glycolide cannot be continued over a long period of time due to the deposition of a mixture containing glycolide on the inside wall of the line or situations in which the amount of recovered glycolide decreases, that is the GAO loss increases, in the rectification step or the subsequent recovery step. The high-boiling-point organic solvent is ordinarily used at a ratio of from 10 to 3,000 parts by mass, preferably from 20 to 2,700 parts by mass, more preferably from 40 to 2,300 parts by mass, and particularly preferably from 50 to 2,000 parts by mass per 100 parts by mass of the GAO. The high-boiling-point organic solvent may be added continuously or in a divided manner during the course of the depolymerization reaction within a range so that the mixture in the depolymerization reaction system preferably forms a substantially uniform liquid phase.

The high-boiling-point organic solvent having a boiling point within a range of 220 to 500° C. at normal pressure is not particularly limited but is preferably selected from a group of compounds having high thermal stability. Examples of the high-boiling-point organic solvent include aromatic alkoxyalkyl carboxylate esters, aliphatic alkoxyalkyl carboxylate esters, polyalkylene glycol ethers, polyalkylene glycol esters, aromatic carboxylic acid esters, aliphatic carboxylic acid esters, aromatic ethers, aliphatic ethers, aromatic phosphoric acid esters, aliphatic phosphoric acid esters, aliphatic imide compounds, aliphatic amide compounds, and aromatic halides, and at least one type selected from the group consisting of these solvents may be used.

[Group (a) Solvents]

Of these high-boiling-point organic solvents having a boiling point within a range of 220 to 500° C. at normal pressure, p-chlorobenzophenone, which is an aromatic halide; phthalic acid bis(alkoxyalkyl esters) such as di(2-methoxyethyl)phthalate, which is an aromatic alkoxyalkyl carboxylate ester; dialkylene glycol dibenzoates such as diethylene glycol dibenzoate, which is a polyelkylene glycol ester; and polyethylene glycol ether such as pentaethylene glycol dimethyl ether, hexaethylene glycol dimethyl ether, and heptaethylene glycol dimethyl ether, which are polyalkylene glycol ethers are particularly preferable solvents from the perspectives of a large solvent power with respect to the GAO, chemical stability, thermal stability, and the like. These high-boiling-point organic solvents having a large solvent power with respect to the GAO are called group (a) solvents.

[Polyalkylene Glycol Ethers]

Particularly preferable group (a) solvents are polyalkylene glycol ethers, and most preferable is at least one type of polyalkylene glycol ether represented by the following formula (1):

$$X-O-(-R-O-)_p-Y \qquad (1)$$

(wherein R is a methylene group or a straight-chain or branched-chain alkylene group having from 2 to 8 carbon atoms, X and Y are each independently a methyl group or an alkyl group or an aryl group having from 2 to 20 carbon atoms, p is an integer of 1 or greater, and when p is 2 or greater, a plurality of R moieties may be the same or different from one another).

In the formula (a), the alkyleneoxy unit (—R—O) is not particularly limited as long as R is a methylene group or a straight-chain or branched-chain alkylene group having from 2 to 8 carbon atoms, but specific examples thereof include polyethylene glycol ethers containing ethyleneoxy units in which R has 2 carbon atoms, polypropylene glycol ethers containing propyleneoxy units in which R has 3 carbon atoms, and polybutylene glycol ethers containing butyleneoxy units in which R has 4 carbon atoms. Of these, polyethylene glycol ethers are particularly preferable in that the raw materials are easy to obtain and the substances are easy to synthesize.

In the polyalkylene glycol ether of the formula (1), the ether groups at both ends (X and Y) are each independently a methyl group or an alkyl group or aryl group having from 2 to 20 carbon atoms, but it is more preferable for both X and Y to be methyl groups or alkyl groups having from 2 to 7 carbon atoms, and the total number of carbon atoms of the alkyl groups contained in the ether groups at both ends is preferably within a range of 2 to 10 and more preferably within a range of 2 to 8. Examples of such alkyl groups include methyl groups, ethyl groups, propyl groups, butyl groups, and pentyl groups. These alkyl groups may be straight-chained or branched. When the number of carbon atoms of the alkyl group is too large, the polarity of the solvent becomes small, and the solvent power with respect to the GAO may decrease. It is preferable for both of the ether groups at both ends (X and Y) to be polyalkylene glycol dimethyl ethers, which are methyl groups.

The properties of a polyalkylene glycol ether change depending on the number of repetitions p of alkyleneoxy units (—R—O—) in the formula (1). In the present invention, a polyalkylene glycol ether in which the number of repetitions p is preferably from 2 to 10, more preferably from 3 to 9, and even more preferably from 4 to 8 is preferably used. When this number of repetitions p is too large, the distribution of the degree of polymerization tends to become too broad at the time of synthesis by means of a polyaddition reaction, and the isolation of polyalkylene glycol ethers with the same number of repeating units becomes difficult.

When the number of repetitions p of alkyleneoxy units (—R—O—) is 2 or greater, a plurality of R moieties may be the same or different from one another. Examples of substances in which a plurality of R moieties are different include substances containing ethyleneoxy units and propyleneoxy units obtained by mixing and reacting ethylene oxide and propylene oxide, but are not limited thereto.

The most preferable polyalkylene glycol ethers in the formula (1) are polyethylene glycol dimethyl ethers in which the alkylene group (R) is an ethylene group and both of the ether groups at both ends (X and Y) are methyl groups. Of these, pentaethylene glycol dimethyl ether, hexaethylene glycol dimethyl ether, and heptaethylene glycol dimethyl ether are more preferable.

[Group (b) Solvents]

In the present invention, high-boiling-point organic solvents having a smaller solvent power with respect to the GAO than group (a) described above may also be used as the high-boiling-point organic solvent having a boiling point within a range of 220 to 500° C. at normal pressure. Examples include aromatic carboxylic acid esters, aliphatic carboxylic acid esters, aromatic halides, aromatic ethers, aliphatic ethers, aromatic phosphoric acid esters, aliphatic phosphoric acid esters, aliphatic imide compounds, aliphatic amide compounds, and polyalkylene glycol ethers having a small solvent power with respect to the GAO and not belonging to the group (a). These high-boiling-point organic solvents are high-boiling-point organic solvents with a small solvent power, wherein the solvent power with which the solvent can dissolve the oligomer alone at a temperature at which a depolymerization reaction of the GAO occurs is roughly at most ⅓, in most cases at most ⅕, and in many cases at most ¹/₁₀ that of the group (a) solvents. These high-boiling-point organic solvents having a small solvent power are called group (b) solvents. These group (b) solvents are ordinarily used as a mixture with the group (a) solvents or are preferably used in combination with the solubilizing agent described below.

[Polyalkylene Glycol Ether Belonging to Group (b) Solvents]

The polyalkylene glycol ether belonging to the group (b) solvents may be a polyalkylene glycol ether represented by the following formula (1):

$$X-O-(-R-O-)_p-Y \qquad (1)$$

However, in this case, the ether groups at both ends (X and Y) are each independently a methyl group or an alkyl group or aryl group having from 2 to 20 carbon atoms, but it is more preferable for both X and Y to be alkyl groups having from 1 to 18 carbon atoms, and the total number of carbon atoms of the alkyl groups contained in the ether groups at both ends is preferably within a range of 11 to 28 and more preferably within a range of 11 to 24. Examples of such alkyl groups include combinations of methyl groups, ethyl groups, propyl groups, butyl groups, pentyl groups, hexyl groups, octyl groups, decyl groups, dodecyl groups, and octadecyl groups. These alkyl groups may be straight-chained or branched.

The properties of a polyalkylene glycol ether belonging to the group (b) solvents change depending on the number of repetitions p of alkyleneoxy units (—R—O—) in the formula (1). The number of repetitions p of a polyalkylene glycol ether having the properties of group (b) is preferably within a range of 2 to 10 and more preferably within a range of 2 to 8.

Examples of polyalkylene glycol ethers belonging to the group (b) solvents include ethylene glycol methyl octadecyl ether, dipropylene glycol dioctyl ether, triethylene glycol butyl octyl ether, and tetraethylene glycol butyl dodecyl ether.

Of the aforementioned group (b) solvents, aromatic carboxylic acid esters, aliphatic carboxylic acid esters, aromatic halides, and aromatic phosphoric acid esters are particularly preferable from the perspectives of the GAO solvent power, chemical stability, thermal stability, and the like. Preferable examples of aromatic carboxylic acid esters include phthalic acid esters such as benzyl butyl phthalate, dibutyl phthalate, diamyl phthalate, and dipropyl phthalate; and benzoic acid esters such as benzyl benzoate. Examples of aliphatic carboxylic acid esters include adipic acid esters such as octyl adipate and sebacic acid esters such as dibutyl sebacate. An example of an aromatic phosphoric acid ester is tricresyl phosphate.

The group (b) solvents described above may only partially dissolve the GAO when the concentration of the GAO is large at a temperature at which a depolymerization reaction of the GAO occurs. On the other hand, many group (b) solvents are inexpensive, and glycolide can be provided with relatively high yield in many cases by increasing the solvent power with respect to the GAO. Therefore, the solubilizing agent described below is ordinarily used in combination to increase the solubility of the GAO with respect to the group (b) solvents. In addition, the solvents may be mixed and used with the group (a) solvents described above to increase the solvent power of the group (b) solvents. The mixing ratio of the two types of solvents is ordinarily (a):(b)=99:1 to 1:99 (mass ratio).

3. Solubilizing Agent

In the method for producing glycolide by depolymerizing a GAO according to the present invention, a solubilizing agent, which may be used to improve the GAO dissolution properties (solubility and/or dissolution rate) with respect to the high-boiling-point organic solvent described above, may be used alone or together with a high-boiling-point organic solvent. That is, the GAO composition may be a GAO composition containing a solubilizing agent.

The solubilizing agent used in the present invention is preferably a compound which satisfies any one or more of the following requirements.

(i) The solubilizing agent may be a compound which is compatible with or soluble in the high-boiling-point organic solvent.

The solubilizing agent is a liquid or a solid at a normal temperature as long as it is a compound which is compatible with or soluble in the high-boiling-point organic solvent preferably used in the present invention.

(ii) The solubilizing agent is a compound having a boiling point of at least 190° C., preferably at least 200° C., more preferably at least 230° C., and even more preferably at least 250° C. at normal pressure.

When the boiling point at normal pressure is less than 190° C., problems may arise in which the solubilizing agent is boiled and vaporized resulting in volatilization from the depolymerization reaction system and the distillation line during the depolymerization reaction or during heating prior to the depolymerization reaction of the GAO. In addition, when a solubilizing agent is used together with a high-boiling-point organic solvent and a compound having a higher boiling point at normal pressure than the boiling point of the high-boiling-point organic solvent at normal pressure is used, the solubilizing agent is not distilled out with glycolide and the high-boiling-point organic solvent, or the amount of distillation is very small, which may be desirable. In this case, compounds having a boiling point of at least 500° C. at normal pressure (including compounds for which the boiling point at normal pressure cannot be confirmed) can be used as solubilizing agents.

(iii) The solubilizing agent is a compound having a functional group such as an OH group, a COOH group, a CONH group, or the like.

(iv) The solubilizing agent is a compound having a greater affinity with the GAO than the high-boiling-point organic solvent.

The affinity of the solubilizing agent and the GAO can be confirmed by the following method. Specifically, a) a mixture of a GAO and a high-boiling-point organic solvent is heated to a temperature of from 230 to 280° C. to form a uniform solution phase; b) a GAO is further added to the mixture and the concentration is increased until the mixture no longer forms a uniform solution phase; and c) a solubilizing agent is added to the mixture and it is virtually observed whether a uniform solution phase is once again formed.

Specific examples of solubilizing agents that can be used in the present invention include monohydric, dihydric, or higher polyhydric alcohols (may be a partially esterified product or a partially etherified product of a polyhydric alcohol), phenols, monohydric, dihydric, or higher polyhydric aliphatic carboxylic acids, aliphatic amides of aliphatic carboxylic acids and amines, aliphatic imides, and polyalkylene glycol ethers having a molecular weight of over 450. These may be respectively used alone or in combinations of two or more types.

Of these, monohydric, dihydric, or higher polyhydric alcohols are particularly effective as solubilizing agents. A monohydric, dihydric, or higher polyhydric alcohol having a boiling point of at least 190° C. at normal pressure can be preferably used as a monohydric, dihydric, or higher polyhydric alcohol. The boiling point of the monohydric, dihydric, or higher polyhydric alcohol used as a solubilizing agent is more preferably at least 200° C., even more preferably at least 230° C., and particularly preferably at least 250° C. Specific examples include aliphatic alcohols such as decanol, tridecanol, decanediol, ethylene glycol, propylene glycol, and glycerin; aromatic alcohols such as naphthyl alcohol; polyalkylene glycol; and polyalkylene glycol monoethers. Of these, a preferable solubilizing agent is a polyalkylene glycol or a polyalkylene glycol monoether.

The polyalkylene glycol is preferably a polyalkylene glycol represented by formula (2):

$$HO-(-R^1-O)_q-H \quad (2)$$

(wherein $R^1$ is a methylene group or a straight-chain or branched-chain alkylene group having from 2 to 8 carbon atoms, q is an integer of 1 or greater, and when q is 2 or greater, a plurality of $R^1$ moieties may be the same or different from one another).

Specific examples of polyalkylene glycols include polyethylene glycol, polypropylene glycol, and polybutylene glycol. These may be respectively used alone or in combinations of two or more types.

The polyalkylene glycol monoether is preferably a polyalkylene glycol monoether represented by formula (3):

$$HO-(-R^2-O)_r-X^1 \quad (3)$$

(wherein $R^2$ is a methylene group or a straight-chain or branched-chain alkylene group having from 2 to 8 carbon atoms, $X^1$ is a hydrocarbon group, r is an integer of 1 or greater, and when r is 2 or greater, a plurality of $R^2$ moieties may be the same or different from one another).

Specific examples of polyalkylene glycol monoethers include polyethylene glycol monoethers such as polyethylene glycol monomethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; a polypropylene glycol monoether in which an ethyleneoxy group is substituted with a propyleneoxy group in the polyethylene glycol monoether; a polybutylene glycol monoether in which an ethyleneoxy group is substituted with a butyleneoxy group in the polyethylene glycol monoether; and other polyalkylene glycol monoethers. A polyethylene glycol monoether preferably has an alkyl group having from 1 to 18 carbon atoms as an ether group. These may be respectively used alone or in combinations of two or more types.

When polyalkylene glycols or polyalkylene glycol monoethers are used as solubilizing agents, practically none of the compounds are distilled out of the depolymerization reaction system due to the high boiling points thereof. Moreover, polyalkylene glycols and polyalkylene glycol monoethers have high GAO solubility, so when these are used as solubilizing agents, the depolymerization reaction of the GAO may proceed rapidly. In addition, when a polyalkylene glycol monoether is used as a solubilizing agent, the cleaning effect of the canister wall (inner wall of the reactor) or the distillation line is particularly excellent.

Further, in the present invention, a non-basic compound having a boiling point of at least 190° C. at normal pressure (excluding monohydric, dihydric, or higher polyhydric alcohols) may be used as a solubilizing agent. As described above, examples of such solubilizing agents include phenols, monohydric, dihydric, or higher polyhydric aliphatic carboxylic acids, aliphatic amides of aliphatic carboxylic acids and amines, aliphatic imides, and polyalkylene glycol ethers having a molecular weight of over 450, and phenol compounds having a boiling point of at least 230° C. at normal pressure can be preferably used. In addition, when a compound having a boiling point within a range of 220 to 500° C. at normal pressure is used as a solubilizing agent, the solubilizing agent also corresponds to a high-boiling-point organic solvent having a boiling point within a range of 220 to 500° C. at normal pressure.

In the present invention, when a solubilizing agent is used together with a high-boiling-point organic solvent having a boiling point within a range of 220 to 500° C. at normal pressure, a polyalkylene glycol ether having a boiling point of over 500° C. at normal pressure can be used as the solubilizing agent. For example, a high-boiling-point, high-molecular-weight polyalkylene glycol ether having higher affinity with the GAO than the polyalkylene glycol ether preferably used as a high-boiling-point organic solvent having a boiling point within a range of 220 to 500° C. at normal pressure and having a boiling point of over 500° C. at normal pressure can be used together as a solubilizing agent. Specific examples of polyalkylene glycol ethers which are suitable as solubilizing agents and have a boiling point of over 500° C. at normal pressure include polyethylene glycol dimethyl ether #500 (number average molecular weight: 500) and polyethylene glycol dimethyl ether #2000 (number average molecular weight: 2,000). These polyalkylene glycol ethers serving as solubilizing agents can be differentiated from the polyalkylene glycol ether serving as a high-boiling-point organic solvent having a boiling point within a range of 220 to 500° C. at normal pressure that is preferably used in the present invention in that the boiling point at normal pressure is over 500° C.

The effects of the solubilizing agent are not sufficiently clear, but it is presumed that the solubilizing agent yields effects such as an effect of transforming the GAO into a substance that is easily dissolved in the polyalkylene glycol ether serving as a high-boiling-point organic solvent having a boiling point within a range of 220 to 500° C. at normal pressure due to interactions with the terminals of the GAO, an effect of severing molecular chains and adjusting the molecular weight due to interactions between the molecular chains of the GAO so as to transform the GAO into a substance that is easily dissolved in the polyalkylene glycol ether serving as a preferable high-boiling-point organic solvent, an effect of changing the polarity of the entire solvent system so as to increase the affinity and the solubility of the GAO, an effect of emulsifying and dispersing the GAO, or a composite effect of these effects. In a method for producing glycolide by depolymerizing a GAO with a weight average molecular weight of at least 10,000, it is often preferable to use a solubilizing agent.

In the method for producing glycolide by depolymerizing a GAO according to the present invention, a solubilizing agent may be used alone as the high-boiling-point organic solvent itself having a boiling point within a range of 220 to 500° C. at normal pressure. The solubilizing agent has a high affinity to the GAO and therefore yields the effect that the depolymerization reaction of the GAO can be initiated under relatively mild conditions. Examples of solubilizing agents that can be used alone as the high-boiling-point organic solvent itself having a boiling point within a range of 220 to 500° C. at normal pressure include polyalkylene glycol monoethers (which may be a substance for which a constant boiling point cannot be measured as long as the mixture contains a component with a boiling point within a range of 220 to 500° C. at normal pressure in an amount of preferably at least 8 mass %, more preferably at least 12 mass %, even more preferably at least 15 mass %, and particularly preferably at least 25 mass %) and phenol compounds. Specifically, polyethylene glycol monomethyl ether or polyethylene glycol monooctyl ether may be preferably used as a polyalkylene glycol monoether, and 4-cumylphenol may be preferably used as a phenol.

In the method for producing glycolide by depolymerizing a GAO according to the present invention, when using a solubilizing agent, a solubilizing agent is ordinarily used at a ratio of from 1 to 500 parts by mass, preferably from 1 to 300 parts by mass, and more preferably from 5 to 250 parts by mass per 100 parts by mass of the GAO. When the ratio of the solubilizing agent that is used is too small, the solubility-improving effect of the solubilizing agent cannot be sufficiently achieved. When the ratio of the solubilizing agent that is used is too large, the recovery of the solubilizing agent becomes expensive, which is not economical.

4. Catalyst

In the method for producing glycolide by depolymerizing a GAO according to the present invention, when the GAO composition is a GAO composition containing a GAO and a high-boiling-point organic solvent having a boiling point within a range of 220 to 500° C. at normal pressure, in particular, the glycolide generation rate or volatilization rate due to depolymerization often becomes large, so it is typically unnecessary to use a catalyst for depolymerization (for example, a tin compound, an antimony compound, or the like). In addition, when producing glycolide using a high-molecular, high-boiling-point organic solvent such as a polyalkylene glycol ether having excellent thermal stability, the catalyst may actually be harmful. However, a catalyst may also be used within a range that does not essentially diminish the present invention.

5. Method for Producing Glycolide

The method for producing glycolide by depolymerizing a GAO according to the present invention is a method for producing glycolide comprising the following steps (1) to (5):

step (1): a step in which a GAO composition is supplied into a reactor and heated to a temperature at which a depolymerization reaction of the GAO occurs at normal pressure or reduced pressure;

step (2) a step in which heating is continued and the depolymerization reaction of the GAO occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

In addition, the method for producing glycolide by depolymerizing a GAO according to the present invention is preferably the aforementioned method for producing glycolide, wherein the step (1) is a step in which a GAO composition containing a GAO and a high-boiling-point organic solvent having a boiling point within a range of 220 to 500° C. at normal pressure is heated to a temperature at which a depolymerization reaction of the GAO occurs at normal pressure or reduced pressure. That is, the method for producing glycolide by depolymerizing a GAO according to the present invention is preferably a method for producing glycolide comprising the following steps (1') to (5):

step (1'): a step in which a GAO composition containing a GAO and a high-boiling-point organic solvent having a boiling point within a range of 220 to 500° C. at normal pressure is supplied into a reactor and heated to a temperature at which a depolymerization reaction of the GAO occurs at normal pressure or reduced pressure;

step (2) a step in which heating is continued and the depolymerization reaction of the GAO occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

Further, the method for producing glycolide by depolymerizing a GAO according to the present invention is preferably the aforementioned method for producing glycolide, wherein the step (3) is a step in which the produced glycolide is distilled out of the reactor together with the high-boiling-point organic solvent. That is, the method for producing glycolide by depolymerizing a GAO according to the present invention is preferably a method for producing glycolide comprising the following steps (1') to (5):

step (1'): a step in which a GAO composition containing a GAO and a high-boiling-point organic solvent having a boiling point within a range of 220 to 500° C. at normal pressure is supplied into a reactor and heated to a temperature at which a depolymerization reaction of the GAO occurs at normal pressure or reduced pressure;

step (2) a step in which heating is continued and the depolymerization reaction of the GAO occurs, thereby producing glycolide;

step (3') a step in which the produced glycolide is distilled out of the reactor together with the high-boiling-point organic solvent;

step (4): a step in which the distillate is introduced into a rectifier and is rectified by means of gas-liquid countercurrent contact; and step (5): a step in which glycolide is recovered.

[Apparatus for Producing Glycolide]

The method for producing glycolide according to the present invention can be implemented using the apparatus for producing glycolide according to the present invention comprising a reactor and a rectifier.

[Glycolic Acid Oligomer Composition]

A GAO composition in the method for producing glycolide by depolymerizing a GAO according to the present invention refers to a composition containing a GAO as an essential component. Accordingly, a GAO composition refers to both a composition substantially formed of only a GAO and a composition containing a GAO and other components such as a high-boiling-point organic solvent having a boiling point within a range of 220 to 500° C. at normal pressure, a solubilizing agent, or the like. Therefore, GAO compositions include GAO compositions that do not contain the aforementioned high-boiling-point organic solvent. In addition, compositions formed of substantially only a GAO include compositions containing a GAO and impurities or the like.

That is, GAO compositions in the present invention typically include GAO compositions having the following specific compositions.

1) A GAO composition formed substantially of only a GAO: as described below, with a method for producing glycolide including a rectification step, it is possible to stably obtain glycolide with a small free acid concentration and high purity.

2) A GAO composition containing a GAO and a high-boiling-point organic solvent having a boiling point within a range of 220 to 500° C. at normal pressure: as described below, with a method for producing glycolide including a rectification step, it is possible to prevent situations in which the production of glycolide cannot be continued over a long period of time due to the deposition of a mixture containing glycolide on the inside wall of the line or situations in which the amount of recovered glycolide decreases, that is the GAO loss increases, in the rectification step or the subsequent recovery step. Since the boiling point at normal pressure is within a range of 220 to 500° C., it is possible to set the depolymerization reaction temperature of the GAO to a high temperature, which makes it possible to increase the glycolide production rate and sufficiently express the effect of rectifying the distilled glycolide by means of gas-liquid countercurrent contact.

2-1) A GAO composition containing a GAO and the group (a) solvent (high-boiling-point organic solvent): a group (a) solvent (high-boiling-point organic solvent) falling under the category of the aforementioned high-boiling-point organic solvent having a boiling point within a range of 220 to 500° C. at normal pressure is a particularly preferable solvent from the perspectives of the solvent power with respect to the GAO, chemical stability, thermal stability, and the like, and such a solvent makes it possible to form a liquid phase substantially uniform with the GAO melt phase. Therefore, as described below, with a method for producing glycolide including a rectification step, it is possible to stably obtain glycolide having a small free acid concentration and high purity over a long period of time.

2-2) A GAO composition containing a GAO and the group (b) solvent (high-boiling-point organic solvent): a group (b) solvent falling under the category of a high-boiling-point organic solvent having a boiling point within a range of 220 to 500° C. at normal pressure is a high-boiling-point organic solvent with a smaller solvent power with respect to the GAO than the group (a) solvents, but there are many inexpensive solvents, and it can be expected that glycolide can be obtained with a relatively high yield and small free acid concentration by increasing the solvent power with respect to the GAO.

2-3) A GAO composition containing a GAO, the group (a) solvent, and the group (b) solvent: the solubility with respect to GAO can be increased, and a liquid phase substantially uniform with the melt phase of the GAO can be formed while using the group (b) solvent, which is often inexpensive. Therefore, as described below, with a method for producing glycolide including a rectification step, it is possible to stably obtain glycolide having a small free acid concentration and high purity glycolide over a long period of time.

3) A GAO composition containing a GAO and the aforementioned solubilizing agent: a solubilizing agent has high affinity to the GAO, so the depolymerization reaction of the GAO can be initialized under relatively mild conditions, and a liquid phase substantially uniform with the melt phase of the GAO can be formed. In addition, an excellent cleaning effect of the canister wall (inner wall of the reactor) or the distillation line can be expected. The solubilizing agent can be used together with the aforementioned high-boiling-point organic solvent having a boiling point within a range of 220 to 500° C. at normal pressure, but it may also be used alone, and it may also be used alone as the high-boiling-point organic solvent itself.

3-1) A GAO composition containing a GAO, the solubilizing agent, and a high-boiling-point organic solvent having a boiling point within a range of 220 to 500° C. at normal pressure:

by also using a solubilizing agent having high GAO solubility in combination, it is possible to form a liquid phase substantially uniform with the melt phase of the GAO, and effects such as the rapid progression of the depolymerization reaction of the GAO and an improvement in the cleaning effect of the canister wall (inner wall of the reactor) or the distillation line can be expected.

3-2) A GAO composition containing a GAO, the group (a) solvent, and the solubilizing agent: by also using a solubilizing agent having high GAO solubility in combination, it is possible to form a liquid phase substantially uniform with the melt phase of the GAO, and effects such as the rapid progression of the depolymerization reaction of the GAO and an improvement in the cleaning effect of the canister wall (inner wall of the reactor) or the distillation line can be expected.

3-3) A GAO composition containing a GAO, the group (b) solvent, and the solubilizing agent: by also using a solubilizing agent having high GAO solubility while using the group (b) solvent, which is often inexpensive, effects such as the rapid progression of the depolymerization reaction of the GAO and an improvement in the cleaning effect of the canister wall (inner wall of the reactor) or the distillation line can be expected.

3-4) A GAO composition containing a GAO, the group (a) solvent, the group (b) solvent, and the solubilizing agent: the GAO solubility is very high, and it is possible to form a liquid phase substantially uniform with the melt phase of the GAO. Effects such as the rapid progression of the depolymerization reaction of the GAO and an improvement in the cleaning effect of the canister wall (inner wall of the reactor) or the distillation line can be expected, and it is possible to stably obtain glycolide having a small free acid concentration and high purity over a long period of time.

[Heating Step]

The method for producing glycolide according to the present invention includes a step in which a GAO composition, preferably a GAO composition containing a GAO and a high-boiling-point organic solvent having a boiling point within a range of 220 to 500° C. at normal pressure, is supplied into a reactor and heated to a temperature at which a depolymerization reaction of the GAO occurs at normal pressure or reduced pressure (heating step). In the heating step, after a GAO composition containing a prescribed amount of a GAO and preferably a high-boiling-point organic solvent having a boiling point within a range of approximately 220 to approximately 500° C. at normal pressure as well as a solubilizing agent, which is added as necessary, is heated as necessary for the purpose of dehydration at normal pressure or reduced pressure, it is heated to a temperature at which the depolymerization of the GAO occurs, that is ordinarily a temperature of from approximately 180 to approximately 320° C., preferably from approximately 190 to approximately 310° C., more preferably from approximately 200 to approximately 300° C., and particularly preferably from approximately 210 to approximately 290° C. Ordinarily, the heating step may be performed at normal pressure, but the heating step is preferably performed in an inert gas atmosphere such as nitrogen gas, and when depressurization is performed, the pressure is within a range of 0.1 to 90 kPa, preferably 0.5 to 50 kPa, and more preferably 1 to 30 kPa.

The GAO forms a melt phase or a solution phase in the heating step. When the GAO composition is a GAO composition containing a GAO and a high-boiling-point organic solvent having a boiling point within a range of 220 to 500° C. at normal pressure, it is possible to increase the glycolide generation and volatilization rate, which is preferable. A compound with high thermal stability is more preferable as the high-boiling-point organic solvent, and as described below, a high-boiling-point organic solvent capable of forming a GAO solution phase is particularly preferable in the heating step.

In the heating step of the method for producing glycolide according to the present invention, the GAO is charged into a reactor (four-neck flask or the like) serving as a depolymerization reaction device for performing a depolymerization reaction in a melt state, a solid state, or after being pulverized into an appropriate particle size as necessary. Preferably, a high-boiling-point organic solvent having a boiling point within a range of 220 to 500° C. at normal pressure is charged into the reactor concurrently with or after the charging of the GAO so as to obtain a GAO composition containing the GAO and the high-boiling-point organic solvent. A solubilizing agent may also be added to the reactor as necessary. In addition, the solubilizing agent may also be used as the high-boiling-point organic solvent itself. A heater (electric heating device or the like) is installed around the reactor, and the temperature of the reactor and the GAO composition inside the reactor can be regulated by adjusting the heating current, for example. A device for distilling out distillation components from the depolymerization reaction system is connected to the reactor, and as described below, a rectifier may be disposed so as to be connected to the reactor.

[Formation of the Solution Phase]

In the heating step, when a GAO composition containing a high-boiling-point organic solvent having a boiling point within a range of 220 to 500° C. at normal pressure is used, it is particularly preferable to use a high-boiling-point organic solvent having compatibility with the GAO and capable of keeping the residual ratio of the melt phase of the GAO to at most 0.5, that is one that forms a liquid phase substantially uniform with the melt phase of the GAO, in the heating phase and one that is compatible with the GAO. In this case, all or most of the GAO dissolves in the high-boiling-point organic solvent in the heating step so that a solution phase of the GAO is substantially obtained. By subjecting the GAO to a depolymerization reaction in the solution state, the production rate of glycolide generated and volatilized from the surface of the GAO composition dramatically increases. Here, the "residual rate of the melt phase" represents the ratio of b/a, where (a) (ml) is the volume of the GAO melt phase formed when F(g) of the GAO is added to a solvent with substantially no solvent power with respect to the GAO such as liquid paraffin and heated to a temperature at which depolymerization occurs, and (b) (ml) is the volume of the GAO melt phase formed when F(g) of the GAO is heated to a temperature at which depolymerization occurs in the solvent in which the residual ratio of the melt phase is to be measured. In addition to compositions in which a high-boiling-point organic solvent is used alone, the residual ratio of the melt phase can also be measured for compositions using both the high-boiling-point organic solvent and a solubilizing agent. The residual rate of the GAO melt phase is preferably at most 0.3, more preferably at most 0.1, and most preferably substantially zero.

[Glycolide Production Step]

After the heating step, a step is performed in which a GAO composition, preferably a GAO composition containing a GAO and a high-boiling-point organic solvent having a boiling point within a range of 220 to 500° C. at normal pressure, is heated further to depolymerize the GAO and to produce glycolide (glycolide production step). The temperature at which the glycolide production step is performed may be the same as or different than the temperature at which the heating step described above is performed. That is, the temperature may be set to a temperature of preferably from approximately 180 to approximately 320° C., more preferably from approximately 200 to approximately 290° C., and particularly preferably from approximately 210 to approximately 280° C. When the reactor is depressurized, the depolymerization reaction of the GAO can be performed without increasing the depolymerization temperature, and the glycolide generation and volatilization rates can be increased, which is preferable. The depolymerization reaction of the GAO is a reversible reaction, so the depolymerization reaction of the GAO progresses efficiently when glycolide is distilled out of the liquid phase. In the glycolide production step, the pressure at which the depolymerization reaction of the GAO is performed may be set within a range of 0.1 to 90 kPa, preferably 0.3 to 50 kPa, more preferably 0.5 to 30 kPa, and even more preferably 0.7 to 10 kPa. Accordingly, in the glycolide production step, the depolymerization reaction is preferably performed at a temperature within a range of 180 to 320° C. and a pressure within a range of 0.1 to 90 kPa. Typically, reducing the pressure of the depolymerization reaction system makes it possible to reduce the temperature at which the glycolide production step and the rectification step described below are performed. As a result, the solvent loss decreases, and the recovery rate of the solvent also increases. Even when the pressure of the depolymerization reaction system is set to less than 0.1 kPa, the effect of improving the efficiency in the glycolide production step does not increase, whereas the costs associated with designing and maintaining the device tend to rise sharply.

[Distillation Step]

In the method for producing glycolide according to the present invention, a step is performed in which the glycolide produced in the glycolide production step is distilled out of the reactor or the like (distillation step). As described above, a device for distilling out the distillation components from the depolymerization reaction system is connected to the reactor, and a rectifier for performing rectification may also be disposed so as to be connected to the reactor. In addition, when rectification is performed separately, a single pipe (glass pipe or the like containing a cooler) for performing simple distillation may be connected.

When the GAO composition is a GAO composition containing a GAO and a high-boiling-point organic solvent having a boiling point within a range of 220 to 500° C. at normal pressure, the distillation step is preferably a step in which the glycolide produced in the glycolide production step is distilled out of the reactor together with the high-boiling-point organic solvent since this makes it possible to prevent glycolide or other low-boiling-point components from being deposited and accumulating on the inner wall surface of the reactor, the inside wall of the rectifier or the single pipe, and the inside wall of the recovery line in the recovery step described below.

[Rectification Step]

The method for producing glycolide according to the present invention is characterized in that it includes a step in which a distillate containing glycolide that is distilled out of the reactor in the distillation step described above, preferably a distillate containing glycolide and the high-boiling-point organic solvent, is introduced into a rectifier and rectified by means of gas-liquid countercurrent contact (rectification step).

Rectification is an operation of performing purification and separation by repeating a gas-liquid countercurrent contact process in which the flow of a liquid generated as a gas is condensed and the flow of a gas that is newly supplied come into contact. That is, rectification is differentiated from distillation, wherein a liquid is obtained by simply condensing a gas that is supplied by means of cooling, in that the reflux of the condensed liquid is repeated, and it is thus an operation that differs from distillation.

Known examples of a rectifier used to perform the rectification step on a distillate containing glycolide, preferably a distillate containing glycolide and the high-boiling-point organic solvent, include rectification columns such as a tray column in which a plurality of trays of different shapes such as a bubble cap, a valve type, a porous plate, a grid, a slit type, or a net type are arranged in the vertical direction, and after gas-liquid contact is performed by infusing airgas arriving from lower levels as bubbles in a liquid accumulated on the trays so as to establish air-liquid equilibrium within each tray, prescribed components are concentrated sequentially from the lower levels toward the upper levels; and a packed column or the like in which gas-liquid contact between a descending liquid and an ascending gas is performed on the surface of a column-like material filled with fillers of various forms such as a ring shape, a saddle shape, a corrugated sheet shape, a planting pin sheet shape, a beam shape, or a winding shape, and gas-liquid equilibrium is established at the position of each filler so as to sequentially concentrate prescribed components from bottom to top. In the present invention, any rectifier such as the rectification columns described above can be used to implement the rectification step for rectifying the produced glycolide by means of gas-liquid countercurrent contact.

The distillate in the glycolide production step for depolymerizing the GAO by continuing heating in the reactor, which is a mixture of the produced glycolide and various volatile components, is introduced into the rectifier for use in the rectification step, and a gas-liquid equilibrium state is achieved with a different composition for each position of the rectifier such as a rectification column, for example, in accordance with the boiling point of each component. In the rectification step of the present invention, the temperature of each portion of the rectifier is adjusted so that the concentration of the target glycolide, that is, the purity of the glycolide, is maximized at a prescribed position of the rectifier such as the uppermost part of the rectification column, for example, and the supply rate from the reactor is adjusted by combining the temperature and the pressure of the reactor. The depolymerization reaction of the GAO is a reversible reaction, so the depolymerization reaction of the GAO progresses efficiently when glycolide is distilled out of the liquid phase. In addition, low-boiling-point volatile components supplied from the reactor are discharged from the system at the initial stage of the rectification step.

The rectification step, that is, the step (4) in which the distillate is introduced into the rectifier and rectified by means of gas-liquid countercurrent contact, is preferably performed with a rectifier disposed so as to be connected to the reactor from the perspectives of the utilization efficiency of thermal energy used to perform the depolymerization reaction of the GAO and the simplification of equipment.

The rectification step can also be performed by a method in which the glycolide produced in the glycolide production step is distilled out the reactor by distillation and temporarily recovered, and after a prescribed amount of the distillate resulting from this distillation is accumulated as necessary, it is introduced into a rectifier disposed separately and rectified. However, this method is not necessarily advantageous from the perspective of the utilization efficiency of thermal energy used to perform the depolymerization reaction of the GAO or the fact that distillation equipment needs to be provided separately.

When the GAO composition is a GAO composition containing a GAO and a high-boiling-point organic solvent having a boiling point within a range of 220 to 500° C. at normal pressure or a GAO composition containing a solubilizing agent added as necessary in the heating step and the glycolide production step described above, the rectification step becomes a step in which the produced glycolide is rectified by means of gas-liquid countercurrent contact in the presence of the high-boiling-point organic solvent, which is preferable from the perspectives of the glycolide production efficiency, the purity of the resulting glycolide, and the thermal energy efficiency.

That is, in this case, the glycolide produced in the glycolide production step and the high-boiling-point organic solvent are both distilled out of the reactor in a gaseous state and introduced into the rectifier, and the rectification step is then performed. In the rectification step executed in the rectifier, the flow of gas newly supplied from the reactor and the flow of liquid condensed inside the rectifier are repeatedly brought into countercurrent contact so that impurities such as low-boiling-point compounds are volatilized and removed at an early stage, and the concentration and purity of the glycolide gradually increase. In addition, it is presumed that the concentration and purity of the glycolide increase due to a process in which, of these impurities, polymerizable components such as glycolic acid are polymerized in the rectification step to form an oligomer, and the oligomer is depolymerized so as to produce glycolide. On the other hand, most of the high-boiling-point organic solvent is separated from glycolide in the rectification step and refluxed to the GAO composition in the reactor for use in the heating step. These effects cannot be expected with distillation, and the present invention utilizes these effects so that the production of glycolide by means of the depolymerization of a GAO can be continued stably for a long period of time.

At this time, the composition of the mixture of the glycolide and the high-boiling-point organic solvent that is distilled out in the rectification step and the high-boiling-point organic solvent can be adjusted by the selection of the high-boiling-point organic solvent, the selection of the structure of the rectifier (number of trays of the tray column, shape or dimensions and packing height of the packing in a packed column, or the like), the degree of vacuum of the rectifier, the adjustment of the reflux ratio and the temperature of each portion, and the adjustment of the supply rate from the reactor by means of a combination of the temperature and pressure of the reactor. Preferably, only glycolide is distilled out in the rectification step, and when the entire high-boiling-point organic solvent is refluxed to the reactor by making adjustments so that the high-boiling-point organic solvent is not distilled out, it is possible to improve the thermal energy efficiency, which makes it possible to reduce the production cost.

[Recovery Step]

After the rectification step in the method for producing glycolide according to the present invention, a step is performed in which glycolide is recovered from a mixture containing the glycolide that is distilled out in the rectification step (recovery step). In the recovery step, glycolide or a distillate from the rectifier such as a rectification column containing glycolide is cooled, and recovery operations for purification by conventional methods may be added as necessary, such as filtration, centrifugation, decantation, phase separation such as liquid-liquid separation, washing or extraction using a poor solvent such as cyclohexane or ether, or crystallization or recrystallization using ethyl acetate or the like. However, with the method for producing glycolide according to the present invention, it is possible to recover glycolide with high purity, so recovery operations such as crystallization are unnecessary or, if implemented, are very easy and simple.

[Solvent Reflux]

In the present invention, at least one of the high-boiling-point organic solvent and the solubilizing agent which is separated in at least one of the rectification step and the recovery step and has a boiling point within a range of 220 to 500° C. at normal pressure may be refluxed to the reactor. The high-boiling-point organic solvent and/or the solubilizing agent that is used as necessary are refluxed to the reactor and returned to the depolymerization reaction system for use in the heating step so that the amount of a new high-boiling-point organic solvent and the like that needs to be added when reusing the high-boiling-point organic solvent is very small.

For example, when the mixture containing the glycolide that is distilled out in the rectification step contains a high-boiling-point organic solvent and a solubilizing agent that is added as necessary, the high-boiling-point organic solvent and/or the solubilizing agent that is used as necessary are preferably separated from the glycolide and refluxed to the reactor to which the GAO composition is supplied so as to be used in the heating step. Since the high-boiling-point organic solvent and/or the solubilizing agent are chemically and thermally stable in the depolymerization reaction, the amounts of a new high-boiling-point organic solvent and/or solubilizing agent that need to be added at the time of reuse are very small. In addition, since the high-boiling-point organic solvent and/or the solubilizing agent have excellent thermal stability, the residue when the distillate is cooled and glycolide is recovered in the recovery step for recovering glycolide from the distillate, that is a phase of the high-boiling-point organic solvent and/or the solubilizing agent when the distillate forms a biphase, can be circulated to the reactor of the depolymerization reaction system.

This will be described in further detail using a recovery step and reflux step involving phase separation by means of the liquid-liquid separation described above as an example. Specifically, a mixture containing the glycolide that is distilled out in the rectification step, the high-boiling-point organic solvent, and/or the solubilizing agent that is used as necessary is cooled with a cooler (condenser), and the glycolide, the high-boiling-point organic solvent, and/or the solubilizing agent are subjected to phase separation in the liquid state so that a glycolide phase is separated and recovered. When the distillate is subjected to phase separation, a glycolide phase is ordinarily formed on the lower layer, and the upper layer becomes a solvent phases (high-boiling-point organic solvent and/or solubilizing agent phase). The glycolide phase of the lower layer can be separated and recovered in the liquid state. In order to perform phase separation on the glycolide and the solvent in the liquid state, the cooling temperature is ordinarily controlled to a range of 85 to 180° C., preferably 85 to 150° C., and more preferably 85 to 120° C. When the cooling temperature is too high, side reactions such as a ring-opening reaction or a polymerization reaction tend to occur in the glycolide phase during the separation operation. When the cooling temperature is too low, it becomes difficult to perform phase separation in the liquid state.

When the depolymerization reaction is continued while controlling the temperature of the distillate with the condenser, the glycolide that is distilled out together with the solvent passes through the solvent phase of the upper layer (high-boiling-point organic solvent and/or solubilizing agent phase) in the form of liquid droplets and is condensed in the glycolide phase of the lower layer.

The separated glycolide phase is further cooled, recovered, and then purified as necessary. With this method, the need to separate a large amount of the solvent (high-boiling-point organic solvent and/or solubilizing agent) from the recovered glycolide is eliminated, which simplifies the operation for separating the solvent and the glycolide.

In addition, in this method, the high-boiling-point organic solvent and/or solubilizing agent phase can be separated from the phase-separated distillate and returned to the depolymerization reaction system. With this method, the need to recover a large amount of the solvent (high-boiling-point organic solvent and/or solubilizing agent) is eliminated, the need to prepare a solvent in excess of the amount determined by the volume of the reactor is eliminated. Accordingly, with this method, the loss of the solvent can be kept to a minimum.

6. Glycolide

The glycolide produced by the method for producing glycolide according to the present invention is a glycolide with high purity and is a highly stable glycolide with a free acid concentration of at most 0.6 mmol/g.

[Purity]

The glycolide obtained by the method for producing glycolide according to the present invention has a purity of at least 10 mass %, preferably at least 15 mass %, more preferably at least 40 mass %, even more preferably at least 60 mass %, particularly preferably at least 70 mass %, and most preferably at least 80 mass %. When the purity of the resulting glycolide is at least 10 mass %, purification such as crystallization or recrystallization is easy, and purification may even be unnecessary depending on the application or the glycolide purity. The upper limit of the glycolide purity is 100 mass % but is ordinarily approximately 99.99 mass % and in many cases approximately 99.95 mass %.

[Measurement of Glycolide Purity]

The purity of glycolide produced by a depolymerization reaction is measured by gas chromatography (GC). First, 200 mg of a glycolide sample and 40 mg of p-chlorobenzophenone (made by Tokyo Chemical Industry Co., Ltd.) serving as an internal standard substance are dissolved in 10 ml of acetone. Next, 2 µl of the solution is collected and injected into a gas chromatography device, and the amount of glycolide is measured. A calibration curve created in advance using glycolide and p-chlorobenzophenone serving as the internal standard substance is used to determine the purity of the glycolide.

<GC Conditions>

Measurement device: "GC-2010" made by Shimadzu Corporation

Column: capillary column TC-17, 0.25 mmϕ×30 mm

Column temperature: 280° C.

Injection temperature: 150° C.

[Free Acid Concentration]

It became clear that glycolide with excellent stability over time can be obtained when the glycolide produced by the method for producing glycolide according to the present invention, that is a depolymerization reaction, has a free acid concentration of at most 0.6 mmol/g, preferably at most 0.55 mmol/g, more preferably at most 0.5 mmol/g, even more preferably at most 0.45 mmol/g, particularly preferably at most 0.4 mmol/g, most preferably at most 0.35 mmol/g, and especially preferably at most 0.3 mmol/g. The lower limit of the free acid concentration of the glycolide produced by the method for producing glycolide according to the present invention is 0 mmol/g since it is preferable for the glycolide to have the smallest free acid concentration possible, but this lower limit may ordinarily be 0.01 mmol/g or greater, or in many cases 0.03 mmol/g or greater.

(Measurement of the Free Acid Concentration of Glycolide)

The free acid concentration in glycolide is measured with the following method. Specifically, 30 mg of a glycolide sample is dissolved in a mixed solvent of 25 ml of acetone and 25 ml of methanol. A methanol solution containing sodium methoxide is dropped into the solution as a neutralizing solution, and the point of neutralization is detected. The free acid concentration present in 1 g of the glycolide sample is calculated from the detected point of neutralization as the number of mmol (units: mmol/g).

7. Method for Purifying Crude Glycolide

The method for producing glycolide according to the present invention can also be applied to a method for purifying crude glycolide. That is, the present invention provides a method for purifying crude glycolide comprising the following steps (i) to (iii):

step (i): a step in which a crude glycolide composition is supplied into a reactor and heated at normal pressure or reduced pressure so that glycolide is distilled;

step (ii): a step in which the distillate is introduced into a rectifier and is rectified by means of gas-liquid countercurrent contact; and step (iii): a step in which glycolide is recovered.

A crude glycolide composition in the method for purifying crude glycolide refers to a composition containing crude glycolide as an essential component. Accordingly, a crude glycolide composition refers to both a composition formed of substantially only crude glycolide, that is a crude glycolide composition containing glycolide and impurities or the like, and a crude glycolide composition containing the crude glycolide and other components such as a high-boiling-point organic solvent or a solubilizing agent. The components described above can be used as the other components such as a high-boiling-point organic solvent or a solubilizing agent.

That is, with the present invention, it is possible to use a method for purifying crude glycolide in which the crude glycolide composition is preferably a crude glycolide composition containing crude glycolide and a high-boiling-point organic solvent having a boiling point within a range of 220 to 500° C. at normal pressure, and the step (i) is a step in which glycolide is distilled out together with the high-boiling-point organic solvent.

In addition, it is possible to use a method for purifying crude glycolide in which the crude glycolide composition is a crude glycolide composition containing a solubilizing agent.

In these cases, the glycolide contained in the crude glycolide composition is distilled out together with the high-boiling-point organic solvent and/or the solubilizing agent and rectified by means of gas-liquid countercurrent contact so as to be purified into glycolide with few impurities, so a distillate containing the recovered glycolide can be cooled with a cooler and thereby phase-separated in the liquid state, which also makes it possible to respectively separate and recover the purified glycolide layer and the high-boiling-point organic solvent and/or solubilizing agent layer.

Since the high-boiling-point organic solvent and/or the solubilizing agent are chemically and thermally stable, the amounts of a new high-boiling-point organic solvent and/or solubilizing agent that is added at the time of reuse are very small. In contrast to conventional purification methods such as sublimation, the scale-up of the method for purifying crude glycolide according to the present invention is easy, and large quantities of crude glycolide can be purified industrially.

Further, the present invention provides the aforementioned method for purifying crude glycolide, in which at least one of the high-boiling-point organic solvent and a solubilizing agent which is separated in at least one of the step (ii) and the step (iii) and has a boiling point within a range of 220 to 500° C. at normal pressure is refluxed to the reactor.

In this case, most of the heat expended for the purification of glycolide, including the distillation of the high-boiling-point organic solvent, can be used as heat required for the rectification step and can be recovered, which saves energy and contributes to the prevention of global warming.

The glycolide that is purified by the method for purifying crude glycolide according to the present invention has little or no impurity content. Specifically, the ratio of glycolide to the total amount of glycolide and impurities can be set to 85 mass % or greater, preferably 90 mass % or greater, and more preferably 95 mass % or greater. Further, this ratio can be set to 99 mass % or greater or, ideally, 100 mass % by means of the selection of the crude glycolide serving as a starting raw material or the selection of the purification conditions.

[Apparatus for Purifying Crude Glycolide]

The method for purifying crude glycolide according to the present invention can be implemented using the apparatus for purifying crude glycolide according to the present invention comprising a reactor and a rectifier.

EXAMPLES

The present invention will be described in further hereinafter using reference examples, working examples and comparative examples, but the present invention is not limited to these working examples. The measurement methods for the physical properties of glycolide are as follows.

[Measurement of Glycolide Purity]

The purity of glycolide produced by a depolymerization reaction was measured by gas chromatography (GC). First, 200 mg of a glycolide sample and 40 mg of p-chlorobenzophenone (made by Tokyo Chemical Industry Co., Ltd.) serving as an internal standard substance were dissolved in 10 ml of acetone. Next, 2 μl of the solution was collected and injected into a gas chromatography device, and the amount of glycolide was measured. A calibration curve created in advance using glycolide and p-chlorobenzophenone serving as the internal standard substance was used to determine the purity of the glycolide.

<GC Conditions>
Measurement device: "GC-2010" made by Shimadzu Corporation
Column: capillary column TC-17, ϕ 0.25 mm×30 mm
Column temperature: 280° C.
Injection temperature: 150° C.

(Measurement of the Free Acid Concentration of Glycolide)

The free acid concentration in the glycolide produced by a depolymerization reaction was measured by the following method. Specifically, 30 mg of a glycolide sample was dissolved in a mixed solvent of 25 ml of acetone and 25 ml of methanol. A methanol solution containing sodium methoxide is dropped into the solution as a neutralizing solution, and the point of neutralization is detected. The free acid concentration present in 1 g of the glycolide sample was calculated from the detected point of neutralization as the number of mmol (units: mmol/g).

(Depolymerization Reaction Device and Distillation Line)

A four-neck flask with a volume of 500 ml was used as a reactor, and a mixing impeller, a thermometer, and a pressure measurement device were disposed thereon to form a depolymerization reaction device. A distillation line was connected to the opening of the top of the flask, and a vacuum line and a receptacle were attached to the outlet of the distillation line. A mantle heater was used to heat the flask of the depolymerization reaction system. A rectifier for performing rectification (packed column or tray column including a cooler) was used as a distillation line in the working examples, and a single pipe for performing simple distillation (glass pipe including a cooler) was used as a distillation line in the comparative examples. In addition, a ribbon heater and a heat insulating material made of glass wool were wrapped around the distillation line to prevent heat radiation.

Reference Example 1

Preparation of GAO

First, 2,500 g of glycolic acid [Glypure (registered trademark) made by Du Pont, Inc.] was charged into an autoclave with a volume of 5.1, and after this was heated from 170° C. to 200° C. over the course of two hours while stirring at normal pressure, a condensation reaction was performed while the water that was produced was distilled out. Next, the pressure inside the canister was reduced to 5.0 kPa, and low-boiling-point components such as the unreacted raw material were distilled out by heating for two hours at a temperature of 200° C. so as to prepare a GAO. The resulting GAO had a weight average molecular weight of 19,000 and a melting point of 218° C.

Working Example 1

A GAO composition containing 150 g of the GAO prepared in Reference Example 1 and 150 g of a hexaethylene glycol dimethyl ether (the group (a) solvent having a boiling point of 356° C. at normal temperature) was charged into the reactor of the depolymerization reaction device and heated to a temperature of 220° C. under reduced pressure conditions of 3.0 kPa in a nitrogen gas atmosphere (heating step). It was visually confirmed that the GAO was uniformly dissolved in the solvent, that no GAO melt phase was present, and that no phase separation had occurred. When the temperature was changed to 237° C. and heating was continued while maintaining the same reduced pressure conditions, the GAO composition boiled and a depolymerization reaction started (glycolide production step), which in turn triggered the distillation of the mixture containing glycolide (distillation step). One hour after distillation began, the cock of the distillation line at the top of the rectifier attached to the depolymerization reaction device [packed column obtained by filling a glass column with an inside diameter of 28 mm having a 1.5 mesh stainless steel screen disposed at the base to a filling height of 480 mm with Dickson packing (⅛ in, made by TO-TOKU Engineering Corporation) while shaking; may be called a "packed column (ϕ 28 mm×480 mm)" hereafter] was closed, and a total reflux operation was performed to stabilize the temperature of the rectifier. When the cock was opened thereafter, glycolide was distilled out of the rectifier and accumulated in the receptacle attached to the distillation line. When distillation was continued for 300 minutes (5 hours), the rectification operation was realized without incident (rectification step). The captured material accumulated in the receptacle was recovered (recovery step), and the product was determined to be concentrated glycolide when analyzed by GC. The purity of the glycolide was 97 mass %, and the free acid concentration in the glycolide was 0.35 mmol/g. The results are shown in Table 1.

Working Example 2

A depolymerization reaction of a GAO was performed in the same manner as in Working Example 1 with the exception that a Snyder 12-level tray column (inside diameter: 20 mm) was used as a rectifier instead of the packed column described above, and the starting conditions of the depolymerization reaction were adjusted to a temperature of 239° C. and a pressure of 3.5 kPa. When distillation was continued for 300 minutes (5 hours), the rectification operation was realized without incident. The captured material accumulated in the receptacle was recovered, and the product was determined to be concentrated glycolide when analyzed by GC. The purity of the glycolide was 97 mass %, and the free acid concentration in the glycolide was 0.35 mmol/g. The results are shown in Table 1.

Working Example 3

A depolymerization reaction of a GAO was performed in the same manner as in Working Example 2 with the exception that a Snyder 7-level tray column (inside diameter: 20 mm) was used as a rectifier instead of a Snyder 12-level tray column (inside diameter: 20 mm), and the starting conditions of the depolymerization reaction were adjusted to a temperature of 243° C. and a pressure of 4.1 kPa. When distillation was continued for 300 minutes (5 hours), the rectification operation was realized without incident. The captured material accumulated in the receptacle was recovered, and the product was determined to be concentrated glycolide when analyzed by GC. The purity of the glycolide was 88 mass %, and the free acid concentration in the glycolide was 0.37 mmol/g. The results are shown in Table 1.

Working Example 4

A depolymerization reaction of a GAO was performed in the same manner as in Working Example 2 with the exception that a GAO composition containing 150 g of the GAO prepared in Reference Example 1 and 150 g of a heptaethylene glycol dimethyl ether (the group (a) solvent having a boiling point of 381° C. at normal pressure) was charged into the reactor of the depolymerization reaction device and heated to a temperature of 258° C. in a nitrogen gas atmosphere under reduced pressure conditions of 3.0 kPa (it was visually confirmed that the GAO was uniformly dissolved in the solvent and that no phase separation had occurred), and that heating was continued while maintaining the reduced pressure conditions and the temperature. When distillation was continued for 300 minutes (5 hours), the rectification operation was realized without incident. The captured material accumulated in the receptacle was recovered, and the product was determined to be concentrated glycolide when analyzed by GC. The purity of the glycolide was 98 mass %, and the free acid concentration in the glycolide was 0.31 mmol/g. The results are shown in Table 1.

Working Example 5

Using the depolymerization reaction device and rectifier (packed column) used in Working Example 1, a GAO composition containing 150 g of the GAO prepared in Reference Example 1 and 150 g of a heptaethylene glycol dimethyl ether (the group (a) solvent having a boiling point of 319° C. at normal pressure) was charged into the reactor of the depolymerization reaction device and heated to a temperature of 220° C. in a nitrogen gas atmosphere under reduced pressure conditions of 5.0 kPa. It was visually confirmed that the GAO was uniformly dissolved in the solvent and that no phase separation had occurred. When heating was continued after the pressure was further reduced to 4.5 kPa and the temperature was changed to 217° C., the GAO composition boiled and a depolymerization reaction started, which in turn triggered the distillation of the mixture containing glycolide. One hour after distillation began, the cock of the distillation line at the top of the rectifier attached to the depolymerization reaction device was closed, and a total reflux operation was performed to stabilize the temperature of the rectifier. When distillation was then continued for 300 minutes (5 hours), the rectification operation was realized without incident. The captured material accumulated in the receptacle was recovered, and the product was determined to be concentrated glycolide when analyzed by GC. The purity of the glycolide was 72 mass %, and the free acid concentration in the glycolide was 0.34 mmol/g. The results are shown in Table 1.

Working Example 6

A depolymerization reaction of a GAO was performed in the same manner as in Working Example 5 with the exception that a rectifier [packed column obtained by filling a glass column with an inside diameter of 20 mm having a 1.5 mesh stainless steel screen disposed at the base to a filling height of 300 mm with Dickson packing (⅛ in, made by TO-TOKU Engineering Corporation) while shaking; may be called a "packed column (φ 20 mm×300 mm)" hereafter] was used as a rectifier instead of a packed column (φ 28 mm×480 mm) and that heating was continued after the starting conditions of the depolymerization reaction were changed to a temperature of 218° C. When distillation was continued for 300 minutes (5 hours), the rectification operation was realized without incident. The captured material accumulated in the receptacle was recovered, and the product was determined to be concentrated glycolide when analyzed by GC. The purity of the glycolide was 20 mass %, and the free acid concentration in the glycolide was 0.38 mmol/g. The results are shown in Table 1.

Working Example 7

A depolymerization reaction of a GAO was performed in the same manner as in Working Example 1 with the exception that a GAO composition containing 150 g of the GAO prepared in Reference Example 1 and 150 g of p-chlorobenzophenone (the group (a) solvent having a boiling point of 332° C. at normal pressure) was charged into the reactor of the depolymerization reaction device and heated to a temperature of 227° C. in a nitrogen gas atmosphere under reduced pressure conditions of 6.0 kPa (it was visually confirmed that the GAO was uniformly dissolved in the solvent and that no phase separation had occurred), and that heating was continued while maintaining the reduced pressure conditions and the temperature. When distillation was continued for 300 minutes (5 hours), the rectification operation was realized without incident. The captured material accumulated in the receptacle was recovered, and the product was determined to be concentrated glycolide when analyzed by GC. The purity of the glycolide was 74 mass %, and the free acid concentration in the glycolide was 0.21 mmol/g. The results are shown in Table 1.

Working Example 8

A depolymerization reaction of a GAO was performed in the same manner as in Working Example 3 with the exception that a GAO composition containing 150 g of the GAO prepared in Reference Example 1 and 150 g of a mixed solvent having a mass ratio of 1:1 of triethylene glycol butyl octyl ether (the group (b) solvent having a boiling point of 354° C. at normal pressure) and polyethylene glycol monomethyl ether [Nippon Nyukazai Co., Ltd., MPG-130H2, solubilizing agent in the form of a mixture containing at least 25 mass % of a component having a boiling point within a range of 220 to 500° C. at normal pressure] was charged into the reactor of the depolymerization reaction device and heated to a temperature of 240° C. in a nitrogen gas atmosphere under reduced pressure conditions of 3.5 kPa (the GAO was mostly dissolved in the solvent, but a slight amount of turbidity was confirmed visually), and that heating was continued after the temperature was changed to 234° C. and the pressure was changed to 3.0 kPa. When distillation was continued for 300 minutes (5 hours), the rectification operation was realized without incident. The glycolide phase in the captured material accumulated in the receptacle was recovered, and the product was determined to be concentrated glycolide when analyzed by GC. The purity of the glycolide was 91 mass %, and the free acid concentration in the glycolide was 0.58 mmol/g. The results are shown in Table 1.

Working Example 9

A depolymerization reaction of a GAO was performed in the same manner as in Working Example 1 with the exception that a GAO composition containing 150 g of the GAO prepared in Reference Example 1 and 150 g of 4-cumylphenol (solubilizing agent having a boiling point of 335° C. at normal pressure) was charged into the reactor of the depolymerization reaction device and heated to a temperature of 230° C. in a nitrogen gas atmosphere under reduced pressure conditions of 3.5 kPa (it was visually confirmed that the GAO was uniformly dissolved in the solvent and that no phase separation had occurred), and that heating was continued while maintaining the reduced pressure conditions and the temperature. When distillation was continued for 300 minutes (5 hours), the rectification operation was realized without incident. The captured material accumulated in the receptacle was recovered, and the product was determined to be concentrated glycolide when analyzed by GC. The purity of the glycolide was 88 mass %, and the free acid concentration in the glycolide was 0.20 mmol/g. The results are shown in Table 1.

Working Example 10

A depolymerization reaction of a GAO was performed in the same manner as in Working Example 6 with the exception that a GAO composition containing 150 g of the GAO prepared in Reference Example 1 and 150 g of the polyethylene glycol monomethyl ether (solubilizing agent) used in Working Example 8 was charged into the reactor of the depolymerization reaction device and heated to a temperature of 230° C. in a nitrogen gas atmosphere under reduced pressure conditions of 1.0 kPa (it was visually confirmed that the GAO was uniformly dissolved in the solvent and that no phase separation had occurred) to initiate a depolymerization reaction, and that the depolymerization reaction was continued while heating so as to raise the temperature to 255° C. while maintaining the reduced pressure conditions. When distillation was continued for 300 minutes (5 hours), the rectification operation was realized without incident. The captured material accumulated in the receptacle was recovered, and the product was determined to be concentrated glycolide when analyzed by GC. The purity of the glycolide was 85 mass %, and the free acid concentration in the glycolide was 0.20 mmol/g. The results are shown in Table 1.

Comparative Example 1

A depolymerization reaction of a GAO was performed in the same manner as in Working Example 1 with the exception that a single pipe was attached as the distillation line connected to the opening at the top of the flask serving as the reactor of the depolymerization reaction device instead of the packed column serving as a rectifier ($\phi$ 28 m×480 mm), and that after the composition was heated to a temperature of 230° under reduced pressure conditions of 3.0 kPa to initiate the depolymerization reaction and to initiate the distillation of the mixture containing glycolide, the depolymerization reaction was continued while heating so as to increase the temperature to 241° C. while maintaining the reduced pressure conditions. The captured material accumulated in the receptacle was recovered, and when analyzed by GC, the purity of the recovered glycolide was 5 mass %, and the free acid concentration in the glycolide was 0.39 mmol/g. The results are shown in Table 1.

Comparative Example 2

A depolymerization reaction of a GAO was performed in the same manner as in Working Example 9 with the exception that a single pipe was attached as the distillation line connected to the opening at the top of the flask serving as the reactor of the depolymerization reaction device instead of the packed column serving as a rectifier ($\phi$ 28 m×480 mm), and that after the composition was heated to a temperature of 233° under reduced pressure conditions of 3.0 kPa to initiate the depolymerization reaction and to initiate the distillation of the mixture containing glycolide, the depolymerization reaction was continued while heating so as to increase the temperature to 244° C. while maintaining the reduced pressure conditions. When distillation was continued for 180 minutes (3 hours), practically no deposited residue of the distillate was observed in the distillation line, but the distillation of glycolide began to diminish, so the depolymerization reaction was ended. The captured material accumulated in the receptacle was recovered, and when analyzed by GC, the purity of the recovered glycolide was 4 mass %, and the free acid concentration in the glycolide was 0.22 mmol/g. The results are shown in Table 1.

Comparative Example 3

A depolymerization reaction of a GAO was performed in the same manner as in Working Example 8 with the exception that a single pipe was attached as the distillation line connected to the opening at the top of the flask serving as the reactor of the depolymerization reaction device instead of the packed column serving as a rectifier ($\phi$ 28 m×480 mm), and that after the composition was heated to a temperature of 230° under reduced pressure conditions of 3.0 kPa to initiate the depolymerization reaction and to initiate the distillation of the mixture containing glycolide, the depolymerization reaction was continued while heating so as to increase the temperature to 244° C. while maintaining the reduced pressure conditions. The glycolide phase in the captured material accumulated in the receptacle was recovered, and when analyzed by GC, the purity of the glycolide was 81 mass %, and the free acid concentration in the glycolide was 1.08 mmol/g. The results are shown in Table 1.

TABLE 1

| Working Examples | Solvent | Boiling point (normal pressure) (°C.) | Depolymerization Reaction solution state | Depolymerization conditions Temperature (°C.) | Depolymerization conditions Pressure (kPa) | Rectifier Size (mm) | Rectifier Number of levels Filler | Recovered glycolide GL purity (mass %) | Recovered glycolide Free acids (mmol/g) |
|---|---|---|---|---|---|---|---|---|---|
| Working Example 1 | Hexaethylene glycol dimethyl ether | 356 | Compatible | 237 | 3.0 | φ 28 × 480 | Dickson packing (⅛ in) | 97 | 0.35 |
| Working Example 2 | Hexaethylene glycol dimethyl ether | 356 | Compatible | 239 | 3.5 | φ 20 | Snyder 12-level | 97 | 0.35 |
| Working Example 3 | Hexaethylene glycol dimethyl ether | 356 | Compatible | 243 | 4.1 | φ 20 | Snyder 7-level | 88 | 0.37 |
| Working Example 4 | Heptaethylene glycol dimethyl ether | 381 | Compatible | 258 | 3.0 | φ 20 | Snyder 12-level | 98 | 0.31 |
| Working Example 5 | Pentaethylene glycol dimethyl ether | 319 | Compatible | 217 | 4.5 | φ 28 × 480 | Dickson packing (⅛ in) | 72 | 0.34 |
| Working Example 6 | Pentaethylene glycol dimethyl ether | 319 | Compatible | 218 | 4.5 | φ 20 × 300 | Dickson packing (⅛ in) | 20 | 0.38 |
| Working Example 7 | p-chlorobenzophenone | 332 | Compatible | 227 | 6.0 | φ 28 × 480 | Dickson packing (⅛ in) | 74 | 0.21 |
| Working Example 8 | Triethylene glycol butyl octyl ether/ polyethylene glycol monomethyl ether (mass ratio: 1:1) | 354/ mixture | Compatible (turbid) | 234 | 3.0 | φ 20 | Snyder 7-level | 91 | 0.58 |
| Working Example 9 | 4- -cumylphenol | 335 | Compatible | 230 | 3.5 | φ 28 × 480 | Dickson packing (⅛ in) | 88 | 0.20 |
| Working Example 10 | Polyethylene glycol monomethyl ether | mixture | Compatible | 230 □ 255 | 1.0 | φ 20 × 300 | Dickson packing (⅛ in) | 85 | 0.20 |
| Comparative Example 1 | Hexaethylene glycol dimethyl ether | 356 | Compatible | 230 □ 241 | 3.0 | Single pipe | | 5 | 0.39 |
| Comparative Example 2 | 4- -cumylphenol | 335 | Compatible | 233 □ 244 | 3.0 | Single pipe | | 4 | 0.22 |
| Comparative Example 3 | Triethylene glycol butyl octyl ether/ polyethylene glycol monomethyl ether (mass ratio: 1:1) | 354/ mixture | Compatible (turbid) | 230 □ 244 | 3.0 | Single pipe | | 81 | 1.08 |

Represents a value measured for the glycolide phase.

It can be seen from Table 1 that in the methods of Working Examples 1 to 10 for producing glycolide by depolymerizing a GAO comprising the following steps (1) to (5):

step (1): a step in which a GAO composition is supplied into a reactor and heated to a temperature at which a depolymerization reaction of the GAO occurs at normal pressure or reduced pressure;

step (2) a step in which heating is continued and the depolymerization reaction of the GAO occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered, the rectification operation can be realized without incident even when distillation is continued for 300 minutes (5 hours), and it is possible to obtain a highly stable glycolide in which the recovered glycolide has a high purity of from 20 to 98 mass % and a small free acid concentration of from 0.20 to 0.58 mmol/g.

In contrast, it can be seen that in the methods for producing glycolide according to Comparative Examples 1 and 2, which do not include the step (4) in which the distillate is introduced into a rectifier and rectified by means of gas-liquid countercurrent contact, the recovered glycolide purity is from 4 to 5 mass %, demonstrating that glycolide with very low purity is obtained. In addition, in the production method of Comparative Example 3, it can be seen that glycolide of poor stability with a free acid concentration of 1.08 mmol/g is obtained. The effect of the method for producing glycolide according to the present invention including the step (4) in which the distillate is rectified by means of gas-liquid countercurrent contact was confirmed from these results.

In addition, it can be seen from the results of Working Examples 2 and 3, in which the number of trays of the tray column was changed, and Working Examples 5 and 6, in which the diameter and filling height of the packed column were changed for the rectifier for implementing the step (4) in which the distillate is introduced into the rectifier and rectified by means of gas-liquid countercurrent contact in the method for producing the glycolide according to the present invention, that the purity of the obtained glycolide or the free acid concentration in the glycolide can be adjusted by changing the mode of the step (4) in which the distillate is introduced into the rectifier and rectified by gas-liquid countercurrent contact by means of the selection of the rectifier or the like.

Further, it can be seen from the method for producing glycolide according to Working Example 8, in which a GAO composition containing a solubilizing agent along with a high-boiling-point organic solvent having a boiling point within a range of 220 to 500° C. at normal pressure as the GAO composition in the step (1), that the combined use of a solubilizing agent increases the purity of the resulting glycolide and makes it possible to reduce the free acid concentration in the glycolide.

Working Example 11

A GAO composition including 150 g of the GAO prepared in Reference Example 1 (not containing a high-boiling-point organic solvent and/or a solubilizing agent) was charged into the reactor of the depolymerization reaction device, and when a depolymerization reaction was initiated by heating the composition to a temperature of 235° C. in a nitrogen gas atmosphere under reduced pressure conditions of 1.0 kPa, a mixture containing glycolide began to be distilled out of the reactor into the rectification device. One hour after the distillation of glycolide from the depolymerization reaction system began, the cock of the distillation line at the top of the rectifier [packed column ($\phi$ 20 mm×300 mm)] attached to the depolymerization reaction device was closed, and a total reflux operation was performed to stabilize the temperature of the rectifier. When the cock was opened thereafter, glycolide was distilled out of the rectifier and began to be accumulated in the receptacle attached to the distillation line. When distillation was continued for 210 minutes (3.5 hours) while maintaining the reduced pressure conditions and increasing the temperature to 278° C., the rectification operation was realized without incident. The captured material accumulated in the receptacle was recovered, and the product was determined to be concentrated glycolide when analyzed by GC. The purity of the glycolide was 96 mass %, and the free acid concentration in the glycolide was 0.5 mmol/g. The results are shown in Table 2.

Comparative Example 4

A depolymerization reaction was performed in the same manner as in Working Example 11 after attaching a single pipe as the distillation line attached to the opening at the top of the flask serving as the depolymerization reaction device instead of the packed column serving as a rectifier. After the composition was heated to a temperature of 237° under reduced pressure conditions of 1.0 kPa as temperature and pressure conditions to initiate the depolymerization reaction and to initiate the distillation of the mixture containing glycolide, the depolymerization reaction was continued while heating so as to increase the temperature to 260° C. while maintaining the reduced pressure conditions, and the distillate was collected. The captured material accumulated in the receptacle was recovered, and when analyzed by GC, the purity of the recovered glycolide was 82 mass %, and the free acid concentration in the glycolide was 1.49 mmol/g. The results are shown in Table 2.

step (2) a step in which heating is continued and the depolymerization reaction of the GAO occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered, and specifically the method of Working Example 11 for producing glycolide in which the GAO composition is a GAO composition that does not contain at least one of a high-boiling-point organic solvent and a solubilizing agent which has a boiling point within a range of 220 to 500° C. at normal pressure, and the distilled glycolide is rectified by means of gas-liquid countercurrent contact using a rectifier [packed column ($\phi$ 20 mm×300 mm)] as the distillation line connected to the reactor for producing glycolide by subjecting the GAO to a depolymerization reaction, even when distillation is continued for 210 minutes (3.5 hours), it is possible to realize rectification operation without incident and to obtain highly stable glycolide in which the recovered glycolide has a high purity of 96 mass % and a low free acid concentration of 0.50 mmol/g.

In contrast, in the production method for glycolide according to Comparative Example 4, which does not include the step (4) in which the distillate is introduced into a rectifier and rectified by means of gas-liquid countercurrent contact, it became clear that the purity of the recovered glycolide was 82 mass % and glycolide of poor stability having lower purity than in Working Example 11 and a free acid concentration of 1.49 mmol/g is obtained. The effect of the method for producing glycolide according to the present invention including the step (4) in which the distillate is introduced into a rectifier and rectified by means of gas-liquid countercurrent contact was confirmed from these results.

Working Example 12

Method for Purifying Crude Glycolide

A crude glycolide composition was prepared by charging 150 g of glycolide (purity: 99.96 mass % or greater), 15 g of glycolic acid (made by Wako Pure Chemical Industries, Ltd., 071-01512), and 100 g of hexaethylene glycol dimethyl ether (high-boiling-point organic solvent having a boiling point of 356° C. at normal pressure) into a reactor (four-neck flask with a volume of 500 ml) connected to the packed column ($\phi$ 28 mm×480 mm) used in Working Example 1 as a rectifier. The glycolide concentration in the crude glycolide composition was 56.6 mass %; the solvent (hexaethylene glycol dimethyl ether) concentration was 37.7 mass %; and the free acid concentration was 0.74 mmol/g. The ratio of glycolide to the

TABLE 2

| Working Examples | Depolymerization conditions | | Rectifier | | Recovered glycolide | |
|---|---|---|---|---|---|---|
| | Temperature (° C.) | Pressure (kPa) | Size (mm) | Number of levels Filler | GL purity (mass %) | Free acids (mmol/g) |
| Working Example 11 | 235 □ 278 | 1.0 | $\phi$ 20 × 300 | Dickson packing (⅛ in) | 96 | 0.50 |
| Comparative Example 4 | 237 □ 260 | 1.0 | | Single pipe | 82 | 1.49 |

It can be seen from Table 2 that in the method of Working Example 11 for producing glycolide by depolymerizing a GAO comprising the following steps (1) to (5):

step (1): a step in which a GAO composition is supplied into a reactor and heated to a temperature at which a depolymerization reaction of the GAO occurs at normal pressure or reduced pressure;

total amount of glycolide and impurities other than the solvent (corresponding to glycolic acid) was 90.9 mass %.

The crude glycolide composition containing crude glycolide and a high-boiling-point organic solvent was heated to a temperature of 180° C. in a nitrogen gas atmosphere. It was visually confirmed that the crude glycolide was uniformly dissolved in the solvent and that no phase separation had occurred. When the pressure was reduced to 3.0 kPa while continuing to heat the crude glycolide composition, the co-distillation of glycolide and the solvent began. The cock of the distillation line at the top of the packed column was closed, and a total reflux operation was performed to stabilize the temperature of the rectifier. When the cock was opened thereafter, glycolide was distilled out of the rectifier (packed column) and accumulated in the receptacle attached to the distillation line. Distillation was performed for approximately 150 minutes (2.5 hours) while continuing to heat the composition until the crude glycolide composition was heated to a temperature of 238° C., and distillation was then ended. No deposition of the distillate was observed on the filler in the rectifier. The amount of the captured material accumulated in the receptacle was 146.6 g, and when analyzed by GC, the glycolide concentration in the captured material was 91.0 mass %, the solvent concentration was 7.9 mass %, and the free acid concentration was 0.18 mmol/g, resulting in a highly stable glycolide. The ratio of glycolide to the total amount of glycolide and impurities other than the solvent was 98.8 mass %. The recovery rate of glycolide was 89%.

INDUSTRIAL APPLICABILITY

The present invention is a method for producing glycolide by depolymerizing a GAO comprising the following steps (1) to (5):

step (1): a step in which a GAO composition is supplied into a reactor and heated to a temperature at which a depolymerization reaction of the GAO occurs at normal pressure or reduced pressure;

step (2) a step in which heating is continued and the depolymerization reaction of the GAO occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

As a result, a method capable of continuing a reaction for a long period of time without any decrease in production efficiency and efficiently and economically producing highly stable glycolide with high purity and a reduced free acid concentration by depolymerizing a GAO is provided, which yields high industrial applicability.

In addition, the present invention is a method for purifying crude glycolide comprising the following steps (i) to (iii):

step (i): a step in which a crude glycolide composition is supplied into a reactor and heated at normal pressure or reduced pressure so that glycolide is distilled;

step (ii): a step in which the distillate is introduced into a rectifier and is rectified by means of gas-liquid countercurrent contact; and step (iii): a step in which glycolide is recovered.

As a result, a method for purifying crude glycolide with which highly stable glycolide can be obtained with high yield, high purity, and a reduced free acid concentration is provided, which yields high industrial applicability.

Further, the present invention is an apparatus for producing glycolide or an apparatus for purifying crude glycolide comprising a reactor and a rectifier, and as a result, an apparatus for producing glycolide or an apparatus for purifying crude glycolide capable of continuing a reaction for a long period of time without any decrease in production efficiency and efficiently and economically producing or purifying highly stable glycolide with high purity and a reduced free acid concentration by depolymerizing a GAO is provided, which yields high industrial applicability.

The invention claimed is:

1. A method for producing glycolide by depolymerizing a glycolic acid oligomer, the method comprising the following steps (1) to (5):

step (1): a step in which a glycolic acid oligomer composition is supplied into a reactor and heated to a temperature at which a depolymerization reaction of the glycolic acid oligomer occurs at normal pressure or reduced pressure;

step (2): a step in which heating is continued and the depolymerization reaction of the glycolic acid oligomer occurs, thereby producing glycolide;

step (3): a step in which the produced glycolide is distilled out of the reactor;

step (4): a step in which the distillate is introduced into a rectifier and is rectified by means of gas-liquid countercurrent contact; and step (5): a step in which glycolide is recovered.

2. The method for producing glycolide according to claim 1, wherein the glycolic acid oligomer composition is a glycolic acid oligomer composition containing a glycolic acid oligomer and a high-boiling-point organic solvent having a boiling point within a range of 220 to 500° C. at normal pressure.

3. The method for producing glycolide according to claim 2, wherein the step (3) is a step in which the produced glycolide is distilled out of the reactor together with the high-boiling-point organic solvent.

4. The method for producing glycolide according to claim 2, wherein the high-boiling-point organic solvent is at least one type selected from the group consisting of aromatic alkoxyalkyl carboxylate esters, aliphatic alkoxyalkyl carboxylate esters, polyalkylene glycol ethers, polyalkylene glycol esters, aromatic carboxylic acid esters, aliphatic carboxylic acid esters, aromatic ethers, aliphatic ethers, aromatic phosphoric acid esters, aliphatic phosphoric acid esters, aliphatic imide compounds, aliphatic amide compounds, and aromatic halides.

5. The method for producing glycolide according to claim 2, wherein the high-boiling-point organic solvent forms a liquid phase substantially uniform with a melt phase of the glycolic acid oligomer in the step (1).

6. The method for producing glycolide according to claim 2, wherein the high-boiling-point organic solvent is at least one type of a polyalkylene glycol ether represented by formula (1):

X—O—(—R—O—)$_p$—Y　　(1)

(wherein R is a methylene group or a straight-chain or branched-chain alkylene group having from 2 to 8 carbon atoms, X and Y are each independently a methyl group or an alkyl group or an aryl group having from 2 to 20 carbon atoms, p is an integer of 1 or greater, and when p is 2 or greater, a plurality of R moieties may be the same or different from one another).

7. The method for producing glycolide according to claim 1, wherein the glycolic acid oligomer composition is a glycolic acid oligomer composition containing a solubilizing agent.

8. The method for producing glycolide according to claim 7, wherein the solubilizing agent is a monohydric or polyhydric alcohol or a phenol compound having a boiling point of at least 190° C. at normal pressure.

9. The method for producing glycolide according to claim 1, wherein in step (2), a depolymerization reaction is performed at a temperature within a range of 180 to 320° C. and a pressure within a range of 0.1 to 90 kPa.

10. The method for producing glycolide according to claim 1, wherein at least one of the high-boiling-point organic solvent and a solubilizing agent which is separated in at least one of the step (4) and the step (5) and has a boiling point within a range of 220 to 500° C. at normal pressure is refluxed to the reactor.

11. The method for producing glycolide according to claim 1, wherein the step (4) is implemented using a rectifier disposed so as to be connected to the reactor.

12. The method for producing glycolide according to claim 1, wherein the glycolic acid oligomer composition is a glycolic acid oligomer composition not containing a high-boiling-point organic solvent having a boiling point within a range of 220 to 500° C. at normal pressure.

* * * * *